United States Patent
Chang et al.

(10) Patent No.: US 9,931,413 B2
(45) Date of Patent: *Apr. 3, 2018

(54) TETRAMERIC CYTOKINES WITH IMPROVED BIOLOGICAL ACTIVITY

(71) Applicant: IBC Pharmaceuticals, Inc., Morris Plains, NJ (US)

(72) Inventors: Chien-Hsing Chang, Downingtown, PA (US); David M. Goldenberg, Mendham, NJ (US); Edmund A. Rossi, Woodland Park, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/291,490

(22) Filed: Oct. 12, 2016

(65) Prior Publication Data

US 2017/0056516 A1 Mar. 2, 2017

Related U.S. Application Data

(60) Division of application No. 14/067,296, filed on Oct. 30, 2013, now Pat. No. 9,498,542, which is a
(Continued)

(51) Int. Cl.

| | |
|---|---|
| *A61K 47/48* | (2006.01) |
| *C07K 16/28* | (2006.01) |
| *C07K 14/56* | (2006.01) |
| *C07K 14/54* | (2006.01) |
| *C07K 14/52* | (2006.01) |
| *C07K 16/00* | (2006.01) |
| *C07K 14/535* | (2006.01) |
| *C07K 14/505* | (2006.01) |
| *C12N 9/12* | (2006.01) |
| *A61K 39/00* | (2006.01) |
| *A61K 38/00* | (2006.01) |

(52) U.S. Cl.
CPC ...... *A61K 47/48423* (2013.01); *A61K 47/481* (2013.01); *A61K 47/48338* (2013.01); *C07K 14/505* (2013.01); *C07K 14/535* (2013.01); *C07K 14/56* (2013.01); *C07K 16/00* (2013.01); *C07K 16/2887* (2013.01); *C12N 9/12* (2013.01); *C12Y 207/11011* (2013.01); *A61K 38/00* (2013.01); *A61K 2039/505* (2013.01); *C07K 2317/24* (2013.01); *C07K 2317/55* (2013.01); *C07K 2317/64* (2013.01); *C07K 2317/732* (2013.01); *C07K 2317/734* (2013.01); *C07K 2317/94* (2013.01); *C07K 2319/00* (2013.01); *C07K 2319/02* (2013.01)

(58) Field of Classification Search
CPC ............ A61K 39/3955; A61K 47/6851; A61K 47/6845; A61K 47/6855; A61K 38/21; A61K 38/212; A61K 38/215; A61K 38/20; A61K 38/2006; A61K 38/2013; A61K 38/202; A61K 38/2026; A61K 38/2033; A61K 38/204; A61K 38/2046; C07K 16/2803; C07K 16/2806; C07K 16/2809; C07K 16/2812; C07K 16/2815; C07K 16/2887; C07K 16/2896; C07K 16/28; C07K 2317/77; C07K 2317/24; C07K 2317/732; C07K 2317/734; C07K 2317/94; C07K 2319/00
See application file for complete search history.

(56) References Cited

U.S. PATENT DOCUMENTS

| | | |
|---|---|---|
| 4,046,722 A | 9/1977 | Rowland |
| 4,699,784 A | 10/1987 | Shih et al. |
| | (Continued) | |

FOREIGN PATENT DOCUMENTS

| | | |
|---|---|---|
| WO | 2000/068248 | 11/2000 |
| WO | 2006/107617 | 10/2006 |
| | (Continued) | |

OTHER PUBLICATIONS

Mecchia et al., "Type I consensus interferon (CIFN) gene transfer into human melanoma cells up-regulates p53 and enhances cisplatin-induced apoptosis: implications for new therapeutic strategies with IFN-alpha", Gene Ther. (2000) 7, 167-179.
Newlon et al., "A Novel Mechanism of PKA Anchoring Revealed by Solution Structures of Anchoring Complexes", EMBO J. 2001; 20:1651-1662.
Newlon et al., "The molecular basis for protein kinase a anchoring revealed by solution NMR", Nature Struct. Biol. 1999; 3:222-227.
Ngo et al., "Computational Complexity, Protein Structure Prediction, and the Levinthal Paradox", the Protein Folding Problem and Tertiary Structure Prediction, Ch. 14, pp. 492-495, (Mertz & Le Grand, Eds.), Birkhauser Boston, 1994.
(Continued)

*Primary Examiner* — Phuong Huynh
(74) *Attorney, Agent, or Firm* — Richard A. Nakashima

(57) ABSTRACT

The present invention concerns methods and compositions for forming cytokine-antibody complexes using dock-and-lock technology. In preferred embodiments, the cytokine-MAb DNL complex comprises an IgG antibody attached to two AD (anchor domain) moieties and four cytokines, each attached to a DDD (docking and dimerization domain) moiety. The DDD moieties form dimers that bind to the AD moieties, resulting in a 2:1 ratio of DDD to AD. The cytokine-MAb complex exhibits improved pharmacokinetics, with a significantly longer serum half-life than either naked cytokine or PEGylated cytokine. The cytokine-MAb complex also exhibits significantly improved in vitro and in vivo efficacy compared to cytokine alone, antibody alone, unconjugated cytokine plus antibody or cytokine-MAb DNL complexes incorporating an irrelevant antibody. In more preferred embodiment the cytokine is G-CSF, erythropoietin or INF-α2b.

6 Claims, 13 Drawing Sheets

Related U.S. Application Data continuation of application No. 13/219,940, filed on Aug. 29, 2011, now Pat. No. 8,597,659, which is a division of application No. 12/752,649, filed on Apr. 1, 2010, now Pat. No. 8,034,352, which is a continuation-in-part of application No. 12/418,877, filed on Apr. 6, 2009, now Pat. No. 7,906,118, which is a continuation-in-part of application No. 12/396,605, filed on Mar. 3, 2009, now Pat. No. 7,858,070, which is a division of application No. 11/633,729, filed on Dec. 5, 2006, now Pat. No. 7,527,787, said application No. 12/418,877 is a continuation-in-part of application No. 11/389,358, filed on Mar. 24, 2006, now Pat. No. 7,550,143, and a continuation-in-part of application No. 11/478,021, filed on Jun. 29, 2006, now Pat. No. 7,534,866, said application No. 12/418,877 is a continuation-in-part of application No. 11/389,358, filed on Mar. 24, 2006, now Pat. No. 7,550,143, and a continuation-in-part of application No. 11/478,021, filed on Jun. 29, 2006, now Pat. No. 7,534,866, said application No. 12/418,877 is a continuation-in-part of application No. 11/925,408, filed on Oct. 26, 2007, now Pat. No. 7,666,400, said application No. 12/418,877 is a continuation-in-part of application No. 12/396,965, filed on Mar. 3, 2009, now Pat. No. 7,871,622, which is a division of application No. 11/391,584, filed on Mar. 28, 2006, now Pat. No. 7,521,056.

(60) Provisional application No. 61/043,932, filed on Apr. 10, 2008, provisional application No. 61/104,916, filed on Oct. 13, 2008, provisional application No. 61/119,542, filed on Dec. 3, 2008, provisional application No. 60/864,530, filed on Nov. 6, 2006, provisional application No. 60/782,332, filed on Mar. 14, 2006, provisional application No. 61/168,657, filed on Apr. 13, 2009, provisional application No. 61/168,668, filed on Apr. 13, 2009, provisional application No. 60/668,603, filed on Apr. 6, 2005, provisional application No. 60/751,196, filed on Dec. 16, 2005.

(56) References Cited

U.S. PATENT DOCUMENTS

| | | | |
|---|---|---|---|
| 4,868,109 A | 9/1989 | Lansdorp et al. | |
| 5,770,198 A | 6/1998 | Coller et al. | |
| 5,871,945 A | 2/1999 | Lockerbie et al. | |
| 6,261,537 B1 | 7/2001 | Klaveness et al. | |
| 6,306,393 B1 | 10/2001 | Goldenberg | |
| 6,524,854 B1 | 2/2003 | Monia et al. | |
| 6,617,135 B1 | 9/2003 | Gillies et al. | |
| 7,060,506 B2 | 6/2006 | Craig | |
| 7,151,164 B2 | 12/2006 | Hansen et al. | |
| 7,521,056 B2 | 4/2009 | Chang et al. | |
| 7,527,787 B2 | 5/2009 | Chang et al. | |
| 7,534,866 B2 | 5/2009 | Chang et al. | |
| 7,541,440 B2 | 6/2009 | Goldenberg et al. | |
| 7,550,143 B2 | 6/2009 | Chang et al. | |
| 7,666,400 B2 | 2/2010 | Chang et al. | |
| 7,858,070 B2 | 12/2010 | Chang et al. | |
| 7,871,622 B2 | 1/2011 | Chang et al. | |
| 7,901,680 B2 | 3/2011 | Chang et al. | |
| 7,906,118 B2 | 3/2011 | Chang et al. | |
| 7,906,121 B2 | 3/2011 | Chang et al. | |
| 7,981,398 B2 | 7/2011 | Chang et al. | |
| 8,003,111 B2 | 8/2011 | Chang et al. | |
| 8,034,352 B2 | 10/2011 | Chang et al. | |
| 8,158,129 B2 | 4/2012 | Chang et al. | |
| 8,163,291 B2 | 4/2012 | Chang et al. | |
| 8,211,440 B2 | 7/2012 | Chang et al. | |
| 8,246,960 B2 | 8/2012 | Chang et al. | |
| 8,277,817 B2 | 10/2012 | Chang et al. | |
| 8,282,934 B2 | 10/2012 | Chang et al. | |
| 8,349,332 B2 | 1/2013 | Chang et al. | |
| 8,435,540 B2 | 5/2013 | Chang et al. | |
| 8,475,794 B2 | 7/2013 | Chang et al. | |
| 8,481,041 B2 | 7/2013 | Chang et al. | |
| 8,491,914 B2 | 7/2013 | Chang et al. | |
| 8,551,480 B2 | 10/2013 | Chang et al. | |
| 8,562,988 B2 | 10/2013 | Chang et al. | |
| 8,597,659 B2 | 12/2013 | Chang et al. | |
| 2003/0198956 A1 | 10/2003 | Makowski et al. | |
| 2003/0232420 A1 | 12/2003 | Braun et al. | |
| 2004/0018587 A1 | 1/2004 | Makowski et al. | |
| 2004/0219131 A1* | 11/2004 | Patten | A61K 38/212 424/85.7 |
| 2005/0003403 A1 | 1/2005 | Rossi et al. | |
| 2006/0210475 A1 | 9/2006 | Goldenberg et al. | |
| 2007/0020259 A1 | 1/2007 | Hansen et al. | |
| 2007/0264265 A1 | 11/2007 | Goldenberg et al. | |
| 2009/0060862 A1 | 3/2009 | Chang et al. | |
| 2009/0111143 A1 | 4/2009 | Goldenberg et al. | |
| 2011/0020273 A1 | 1/2011 | Chang et al. | |
| 2011/0064754 A1 | 3/2011 | Taylor et al. | |
| 2011/0143417 A1 | 6/2011 | Chang et al. | |
| 2011/0158905 A1 | 6/2011 | Goldenberg et al. | |
| 2011/0189083 A1 | 8/2011 | Chang et al. | |
| 2012/0093769 A1 | 4/2012 | Chang et al. | |
| 2012/0196346 A1 | 8/2012 | Chang et al. | |
| 2012/0276100 A1 | 11/2012 | Chang et al. | |
| 2012/0276608 A1 | 11/2012 | Chang et al. | |
| 2013/0078183 A1 | 3/2013 | Chang et al. | |
| 2013/0109073 A1 | 5/2013 | Chang et al. | |
| 2013/0164816 A1 | 6/2013 | Chang et al. | |
| 2013/0177532 A1 | 7/2013 | Chang et al. | |
| 2013/0217091 A1 | 8/2013 | Chang et al. | |
| 2013/0295005 A1 | 11/2013 | Chang et al. | |

FOREIGN PATENT DOCUMENTS

| | | |
|---|---|---|
| WO | 2006/107786 | 10/2006 |
| WO | 2007/075270 | 7/2007 |
| WO | 2008/033413 | 3/2008 |

OTHER PUBLICATIONS

Nordstrom et al., "First Bispecific Antibody Immunocytokine (Anti-CD20/HLA-DR-Interferon-α2b) is Highly Toxic for Human Lymphoma Cells in Vitro", 2009 ASH Annual Meeting Abstracts, Nov. 20, 2009; 114(22):675, Abstract # 1695.

Osborn et al., "Pharmacokinetic and Pharmacodynamic Studies of a Human Serum Albumin-Interferon-α Fusion Protein in Cynomolgus Monkeys", J. Pharmacol. Exp. Ther. 303(2):540-548 (2002).

Oyen et al., "Human testis cDNA for the regulatory subunit RIIα of cAMP-dependent protein kinase encodes an alternate amino-terminal region", FEBS Letters 246:57-64, 1989.

Ozzello et al., "Conjugation of interferon alpha to a humanized monoclonal antibody (HuBrE-3vl) enhances the selective localization and antitumor effects of interferon in breast cancer xenografts", Breast Cancer Res. Treat. 48: 135-147 (1998).

Paquette et al., "Interferon-α and granulocyte-macrophage colony-stimulating factor differentiate peripheral blood monocytes into potent antigen-presenting cells", J. Leukoc. Biol. 64:358-367; 1998.

Pelham et al., "Interferon-α conjugation to human osteogenic sarcoma monoclonal antibody 791T/36", Cancer Immunol. Immuother. 1983;15(3):210-216.

Pepinsky et al., "Improved Pharmacokinetic Properties of a Polyethylene Glycol-Modified Form of Interferon-β-1a with Preserved in Vitro Bioactivity", Pharmacol. Exp. Ther. 2001; 297(3):1059-1066.

Pilling et al., "Interferon-β mediates stromal cell rescue of T cells from apoptosis", Eur. J. Immunol. 29:1041-1050 (1999).

Rabjohn et al., "Molecular Cloning and Epitope Analysis of the Peanut Allergen Ara h 3", J. Clinical Investigation 103 (4):535-542 (1999).

(56) References Cited

OTHER PUBLICATIONS

Raefsky et al., "Studies of Interferon as a regulator of hematopoietic cells proliferation", J. Immunol. 135 (4):2507-2512 (1985).
Riemer et al., "Matching of trastuzumab (Herceptin) epitope mimics onto the surface of Her-2/neu—a new method of epitope definition", Mol Immunol. May 2005;42(9):1121-4.
Rose et al., "Structural basis of dimerization, coactivator recognition and MODY3 mutations in Hnf-1α", Nature Struct. Biol. 2000; 7:744-748.
Rosendahl et al., "A Long-Acting, Highly Potent Interferon α-2 Conjugate Created Using Site-Specific PEGylation", Bioconjugate Chem. 2005;16:200-207.
Rossi et al., "Novel Designs of Multivalent Anti-CD20 Humanized Antibodies as Improved Lymphoma Therapeutics", Cancer Res. 68:8384-92, 2008.
Rossi et al., "Stably tethered multifunctional structures of defined composition made by the dock and lock method for use in cancer targeting", Proc. Natl. Acad. Sci. Epub Apr. 24, 2006, vol. 103, No. 18, pp. 6841-6846.
Rossi et al., "CD20-targeted tetrameric interferon-α, a novel and potent immunocytokine for the therapy of B-cell lymphomas", Blood 2009;114:3864-3871.
Rossi et al., "A veltuzumab-IFNα2b conjugate with potent in vitro and in vivo anti-lymphoma activity", Proceedings of the American Association for Cancer Research, Apr. 2009;50:783-784, Abstract # 3237.
Rustandi et al., "The Ca2+-Dependent Interaction of S100B(ββ) with a Peptide Derived from p53", Biochemistry 1998; 37: 1951-1960.
Sabaawy et al., "Enhancement of 5-fluorouracil cytotoxicity on human colon cancer cells by retrovirus-mediated interferon-α gene transfer", Int. J. Oncol. Jun. 1999; 14(6):1143-51.
Salles et al., "Rituximab combined with chemotherapy and interferon in follicular lymphoma patients: results of the GELA-GOELAMS FL2000 study", Blood 2008; 112:4824-4831.
Santini et al., "Type I Interferon as a Powerful Adjuvant for Monocyte-derived Dendritic Cell Development and Activity In Vivo and in Hu-PBL-SCID Mice", J. Exp. Med. 191(10)1777-1788 (2000).
Scott et al., "Type II Regulatory Subunit Dimerization Determines the Subcellular Localization of the cAMP-dependent Protein Kinase", J. Biol. Chem. 265:21561-66 (1990).
Scott et al., "Cyclic nucleotide-dependent protein kinases", Pharmacol. Ther. 1991;50(1):123-45.
Seffernick et al., "Melamine Deaminase and Atrazine Chlorohydrolase: 98 Percent Identical but Functionally Different", J. Bacteriol. 183(8):2405-2410 (2001).
Sharkey et al., "Improved Therapeutic Results by Pretargeted Radioimmunotherapy of Non-Hodgkin's Lymphoma with a New Recombinant, Trivalent, Anti-CD20, Bispecific Antibody", Cancer Res. 68:5282-90, 2008.
Sharkey et al., "Metastatic Human Colonic Carcinoma: Molecular Imaging with Pretargeted SPECT and PET in a Mouse Model", Radiology 246:497-507, 2008.
Sidky and Borden, "Inhibition of Angiogenesis by Interferons: Effects on Tumor- and Lymphocyte-induced Vascular Responses", Cancer Res. 47:5155-5161, Oct. 1, 1987.
Stancovski et al., "Mechanistic aspects of the opposing effects of monoclonal antibodies to the ERBB2 receptor on tumor growth", Proc Natl Acad Sci U S A. Oct. 1, 1991;88(19):8691-5.
Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma", Clin. Cancer Res. vol. 10, 2868-2878, Apr. 15, 2004.
Stein et al., "Characterization of a humanized IgG4 anti-HLA-DR monoclonal antibody that lacks effector cell functions but retains direct antilymphoma activity and increases the potency of rituximab", Blood 2006;108:2736-2744.
Stokka et al., "Characterization of A-kinase-anchoring disruption using a solution-based assay", Biochem. J. (2006) 400, 493-499.
Stryer et al., "Levels of Structure in Protein Architecture", Biochemistry, 3rd Ed., pp. 31-33, W.H. Freeman & Co., New York, 1988.
Takaoka et al., Integration of interferon-α/β signalling to p53 responses in tumour suppression and antiviral defence, Nature Jul. 31, 2003;424(6948):516-23.
Taylor, S., "cAMP-dependent Protein Kinase", J. Biol. Chem. 1989;264(15):8443-8446.
Walsh et al., "An Adenosine 3', 5'-Monophosphate-dependant Protein Kinase from Rabbit Skeletal Muscle", J. Biol. Chem. 243(13):3763-3774 (1968).
Weck et al., "Comparison of the Antiviral Activities of Various Cloned Human Interferon-α Subtypes in Mammalian Cell Cultures", J. Gen. Virol. (1981), 57, 233-237.
Winkler et al., "Changing the Antigen Binding Specificity by Single Point Mutations of an Anti-p24 (HIV-1) Antibody", J. Immunol. 165:4505-14, 2000.
Witkowski et al., "Conversion of a β-Ketoacyl Synthase to a Malonyl Decarboxylase by Replacement of the Active-Site Cysteine with Glutamine", Biochemistry 38(36):11643-50 (1999).
Wong et al., "AKAP Signalling Complexes: Focal Points in Space and Time", Nat. Rev. Mol. Cell Biol. 12:959-70 (2004).
Zhu et al., "Inhibition of tumor growth and metastasis by targeting tumor-associated angiogenesis with antagonists to the receptors of vascular endothelial growth factor", Invest. New Drugs 17:195-212, 1999.
Abbas et al., Cellular and Molecular Immunology, W.B. Saunders Comp. 1991, p. 43.
Alto et al., "Bioinformatic design of A-kinase anchoring protein-in silico: a potent and selective peptide antagonist of type II protein kinase A anchoring", Proc. Natl. Acad. Sci USA Apr. 15, 2003; 100(8):4445-50.
Backer et al., "Self-Assembled "Dock and Lock" System for Linking Payloads to Targeting Proteins", Bioconjugate Chem., 2006, 17(4):912-919.
Baillie et al., "Compartmentalisation of phospodiesterases and protein kinase A: opposites attract", FEBS Letters 2005; 579:3264-3270.
Banky et al., "Dimerization/Docking Domain of the Type Iα Regulatory Subunit of cAMP-dependent Protein Kinase", J. Biol. Chem. 273:35048-55, 1998.
Basu et al., "Structure-Function Engineering of Interferon-β-1 b for Improving Stability, Solubility, Potency, Immunogenicity, and Pharmacokinetic Properties by Site-Selective Mono-PEGylation", Bioconjugate Chem. 2006; 17:618-630.
Belardelli et al., "Interferon-alpha in tumor immunity and immunotherapy", Cytokine Growth Factor Rev. 13(2):119-134 (2002).
Belardelli et al., "International Meeting on Cancer Vaccines: How Can We Enhance Efficacy of Therapeutic Vaccines?", Cancer Res. 64:6827-6830 (2004).
Belardelli and Gresser, "The neglected role of type I interferon in the T-cell response: implications for its clinical use", Immunol. Today 17(8):369-72 (1996).
Biron et al., "Natural killer cells in antiviral defense: function and regulation by innate cytokines", Annu. Rev. Immunol. 17:189-220 (1999).
Brunda et al., "Modulation of Murine Natural Killer Cell Activity in Vitro and in Vivo by Recombinant Human Interferons", Cancer Res. 44:597-601 (1984).
Burns-Hamuro et al., "Distinct interaction modes of an AKAP bound to two regulatory subunit isoforms of protein Kinase A revealed by amide hydrogen/deuterium exchange", Protein Science (2005), 14:2982-2992.
Carr et al., "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).

(56) References Cited

OTHER PUBLICATIONS

Carr et al., "Identification of Sperm-specific Proteins That Interact with A-kinase Anchoring Proteins in a Manner Similar to the Type II Regulatory Subunit of PKA", J. Biol. Chem. 276(20):17332-17338 (2001).
Carrero et al., "Lymphocytes are detrimental during the early innate immune response against Listeria monocytogenes", J. Exp. Med. 203(4):933-940 (2006).
Chang et al., "The Dock and Lock Method: A Novel Platform Technology for Building Multivalent, Multifunctional Structures of Defined Composition with Retained Bioactivity", Clin. Cancer Res. Sep. 15, 2007;13(18 Suppl), pp. 5586-5591.
Chmura et al., "Antibodies with infinite affinity", Proc. Natl. Acad. Sci. USA 98(15):8480-8484 (2001).
Colledge et al., "AKAPs: from structure to function", Trends Cell Biol. 6:216-21 (1999).
Corbin et al., "Regulation of Adenosine 3',5'-Monophosphate-dependent Protein Kinase", J. Biol. Chem. 248:1813-21 (1973).
Dhalluin et al., "Structural and Biophysical Characterization of the 40 kDa PEG-Interferon-α2a and Its Individual Positional Isomers", Bioconjugate Chem. 2005;16:504-517.
Dodart et al., "Immunotherapy for Alzheimer's Disease: will vaccination work?", Trends Mol. Med. 9(3):85-87 (2003).
Doherty et al., "Site-Specific PEGylation of Engineered Cysteine Analogues of Recombinant Human Granulocyte-Macrophage Colony-Stimulating Factor", Bioconjugate Chem. 2005;16:1291-1298.
Ferrantini et al., "IFN-α1 Gene Expression into a Metastatic Murine Adenocarcinoma (TS/A) Results in CD8+ T Cell-Mediated Tumor Rejection and Development of Antitumor Immunity", J. Immunol. 153:4604-15 (1994).
Ferrantini et al., "Interferon-α and cancer: Mechanisms of action and new perspectives of clinical use", Biochimie 89: 884-893 (2007).
Gillies et al., "High-level expression of chimeric antibodies using adapted cDNA variable region cassettes", J. Immunol. Methods 125 (1989) 191-202.
Glennie et al., "Mechanisms of killing by anti-CD20 monoclonal antibodies", Mol. Immunol. 44:3823-3837 (2007).
Gold et al., "A Novel Bispecific, Trivalent Antibody Construct for Targeting Pancreatic Carcinoma", Cancer Res. 68:4819-26, 2008.
Gold et al., "Molecular Basis of AKAP Specificity for PKA Regulatory Subunits", Mol. Cell Nov. 3, 2006;24(3):383-95.
Goldenberg et al., "Multifunctional Antibodies by the Dock-and-Lock Method for Improved Cancer Imaging and Therapy by Pretargeting", J. Nucl. Med. 49:158-63, 2008.
Goldenberg et al., "Properties and structure-function relationships of veltuzumab (hA20), a humanized anti-CD20 monoclonal antibody", Blood 113:1062-70 (2009).
Goodson and Katre, "Site-Directed PEGylation of Recombinant Interleukin-2 at its Glycosylation Site", Nat. Biotechnology Apr. 1990;8(4):343-6.
Grace et al., "Site of Pegylation and Polyethylene Glycol Molecule Size Attenuate Interferon-α Antiviral and Antiproliferative Activities through the JAK/STAT Signaling Pathway", J. Biol. Chem. 2005;280(8):6327-6336.
Grimley et al., "Prolonged STAT1 Activation Related to the Growth Arrest of Malignant Lymphoma Cells by Interferon-α", Blood 91(8):3017-27 (1998).
Gutterman et al., "Leukocyte Interferon-Induced Tumor Regression in Human Metastatic Breast Cancer, Multiple Myeloma, and Malignant Lymphoma", Ann. Intern. Med. 93(3):399-406 (1980).
Gutterman et al., "Cytokine therapeutics: Lessons from interferon α", Proc. Natl. Acad. Sci. USA 91:1198-205 (1994).
Harris and Chess, "Effect of pegylation on pharmaceuticals", Nat. Rev. Drug. Discov. 2:214-221 (2003).
Hausken et al., "Mutational Analysis of the A-Kinase Anchoring Protein (AKAP)-binding Site on RII", J. Biol. Chem. 271:29016-22 (1996).

Hodneland et al., "Selective immobilization of proteins to self-assembled monolayers presenting active site-directed capture ligands", Proc. Natl. Acd. Sci. USA 2002; 99:5048-5052.
Huang et al., "Targeting IFN-α to B Cell Lymphoma by a Tumor-Specific Antibody Elicits Potent Antitumor Activities", J. Immunol. 179:6881-88 (2007).
Hundsrucker et al., "High-affinity AKAP7δ-protein kinase A interaction yields novel protein kinase A-anchoring disruptor peptides", Biochem. J. (2006) 396, 297-306.
Kimby et al., "Long-term molecular remissions in patients with indolent lymphoma treated with rituximab as a single agent or in combination with interferon alpha-2a: A randomized phase II study from the Nordic Lymphoma Group", Leuk. Lymphoma 49(1):102-112 (2008).
Kinderman et al., "A Dynamic Mechanism for AKAP Binding to RII Isoforms of cAMP-Dependent Protein Kinase", Mol. Cell 24(3):397-408 (2006).
Kinstler et al., "Characterization and Stability of N-terminally PEGylated rhG-CSF", Pharm. Res. 1996;13(7):996-1002.
Kramer et al., "Cell and virus sensitivity studies with recombinant human alpha interferons", J. Interferon. Res. 3(4):425-35 (1983).
Le Bon et al., "Type I Interferons Potently Enhance Humoral Immunity and Can Promote Isotype Switching by Stimulating Dendritic Cells In Vivo", Immunity 14:461-470 (2001).
Lee et al., "Solid-Phase PEGylation of Recombinant Interferon α-2a for Site-Specific Modification: Process Performance, Characterization, and in Vitro Bioactivity", Bioconjugate Chem. 2007; 18:1728-34.
Lohmann et al., "High-affinity binding of the regulatory subunit (RII) of cAMP-dependent protein kinase to microtubule-associated and other cellular proteins", Proc. Natl. Acad. Sci. USA 81:6723-27 (1984).
Luft et al., "Type I IFNs Enhance the Terminal Differentiation of Dendritic Cells", J. Immunol. 161:1947-1953 (1998).
Mason, A., "Functional Analysis of the Cysteine Residues of Activin A", Mol. Endocrinol. 8:325-32, 1994.
Matarrese et al., "Type I Interferon Gene Transfer Sensitizes Melanoma Cells to Apoptosis via a Target Activity on Mitochondrial Function", Am. J. Pathol. 2002, 160(4):1507-1520.
Cardillo et al., "Targeting both IGF-1R and mTOR synergistically inhibits growth of renal cell carcinoma in vitro", BMC Cancer. Apr. 1, 2013;13:170.
Chang et al., "A new method to produce monoPEGylated dimeric cytokines shown with human interferon-α2b", Bioconjug Chem. Oct. 21, 2009;20(10)1899-907.
Chang et al., "A novel class of anti-HIV agents with multiple copies of enfuvirtide enhances inhibition of viral replication and cellular transmission in vitro", PLoS One. 2012;7(7):e41235.
Chang et al., "Evaluation of a novel hexavalent humanized anti-IGF-1R antibody and its bivalent parental IgG in diverse cancer cell lines", PLoS One. 2012;7(8):e44235.
Coleman, PM., "Effects of amino acid sequence changes on antibody-antigen interactions", Res Immunol. Jan. 1994;145(1):33-6.
Golay et al., "Mechanism of action of therapeutic monoclonal antibodies: promises and pitfalls of in vitro and in vivo assays", Arch Biochem Biophys. Oct. 15, 2012;526(2):146-53.
Goldenberg et al., "Cancer Imaging and Therapy with Bispecific Antibody Pretargeting", Update Cancer Ther. Mar. 2007;2(1):19-31.
Govindan et al., "Designing immunoconjugates for cancer therapy", Expert Opin Biol Ther. Jul. 2012;12(7):873-90.
Hay et al., "Clinical development success rates for investigational drugs", Nat Biotechnol. Jan. 2014;32(1):40-51.
Jubala et al., "CD20 expression in normal canine B cells and in canine non-Hodgkin lymphoma", Vet Pathol. Jul. 2005;42(4):468-76.
Kang et al., "HMGB1 in cancer: good, bad, or both?", Clin Cancer Res. Aug. 1, 2013;19(15):4046-57.
Lange et al., "HMGB1: the jack-of-all-trades protein is a master DNA repair mechanic", Mol Carcinog. Jul. 2009;48(7):571-80.
Lederman et al., "A single amino acid substitution in a common African allele of the CD4 molecule ablates binding of the monoclonal antibody, OKT4", Mol Immunol. Nov. 1991;28(11):1171-81.

(56) References Cited

OTHER PUBLICATIONS

Liu et al., "Trop-2-targeting tetrakis-ranpimase has potent antitumor activity against triple-negative breast cancer", Mol Cancer. Mar. 10, 2014;13:53.
Lotze et al., "High-mobility group box 1 protein (HMGB1): nuclear weapon in the immune arsenal", Nat Rev Immunol. Apr. 2005;5(4):331-42.
Paul, W., ed., Fundamental Immunology, 3rd Ed., Raven Press, New York, 1993, p. 292-295.
Rossi et al., "Hexavalent bispecific antibodies represent a new class of anticancer therapeutics: 1. Properties of anti-CD20/CD22 antibodies in lymphoma", Blood. Jun. 11, 2009;113(24):6161-71.
Rossi et al., "The dock-and-lock method combines recombinant engineering with site-specific covalent conjugation to generate multifunctional structures", Bioconjug Chem. Mar. 21, 2012;23(3):309-23.
Rossi et al., "Complex and defined biostructures with the dock-and-lock method", Trends Pharmacol Sci. Sep. 2012;33(9):474-81.
Rossi et al., "Optimization of multivalent bispecific antibodies and immunocytokines with improved in vivo properties", Bioconjug Chem. Jan. 16, 2013;24(1):63-71.
Rossi et al., "A new class of bispecific antibodies to redirect T cells for cancer immunotherapy", MAbs. Mar.-Apr. 2014;6(2):381-91.
Rudikoff et al., "Single amino acid substitution altering antigen-binding specificity", Proc Natl Acad Sci U S A. Mar. 1982;79(6):1979-83.
Sharkey et al., "Improved cancer therapy and molecular imaging with multivalent, multispecific antibodies", Cancer Biother Radiopharm. Feb. 2010;25(1):1-12.

* cited by examiner

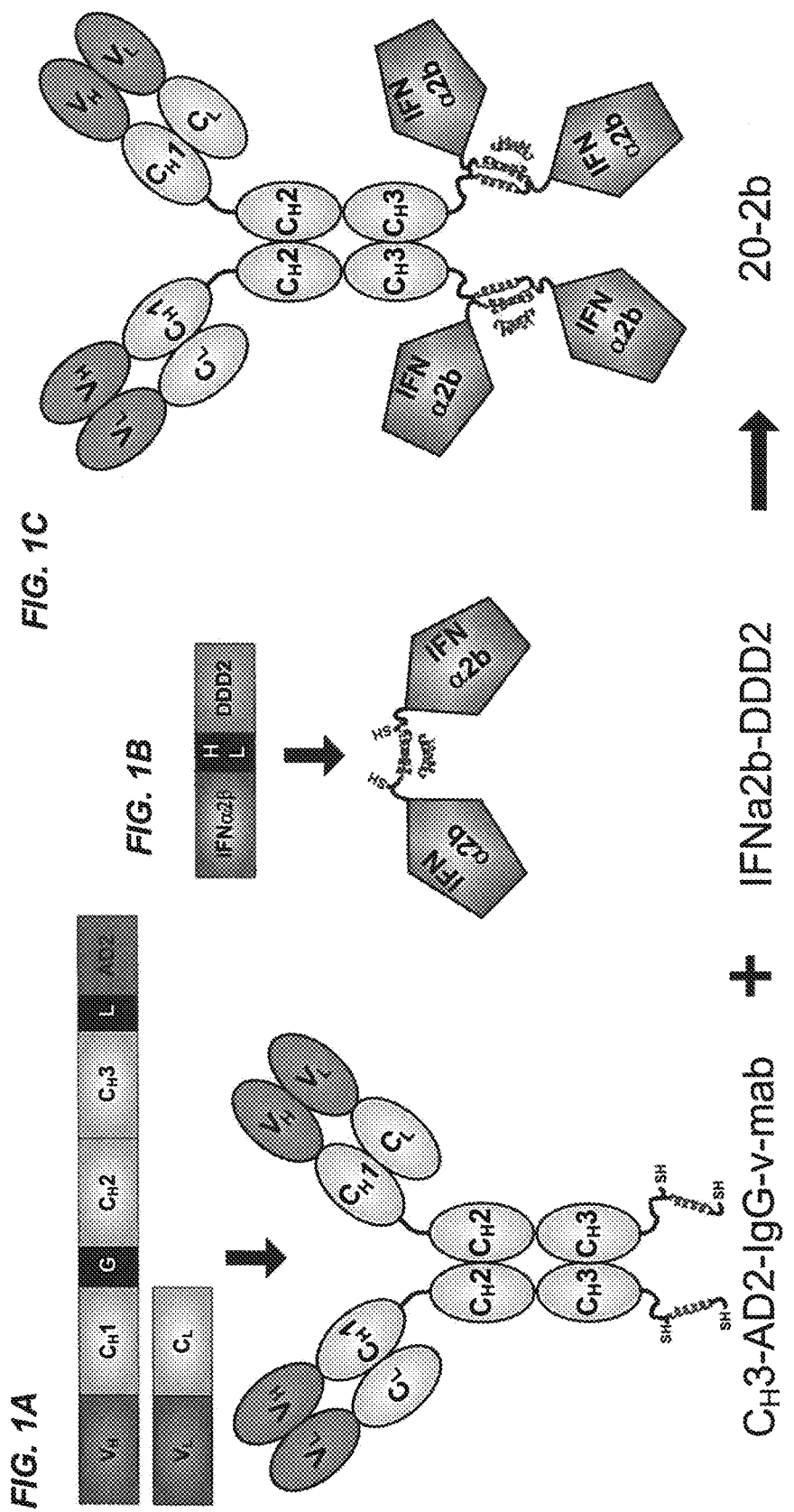

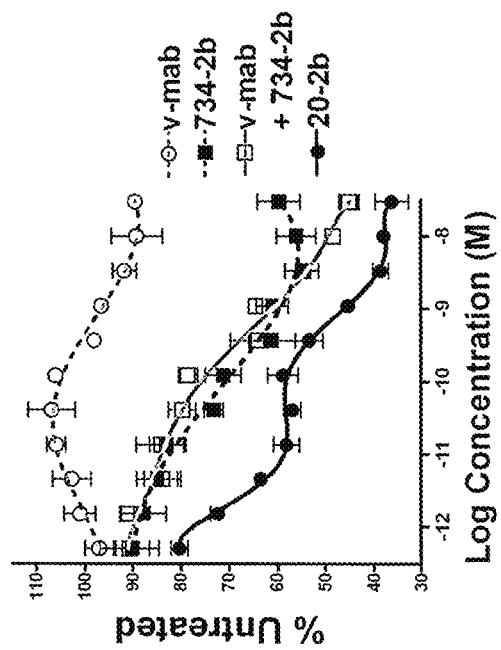
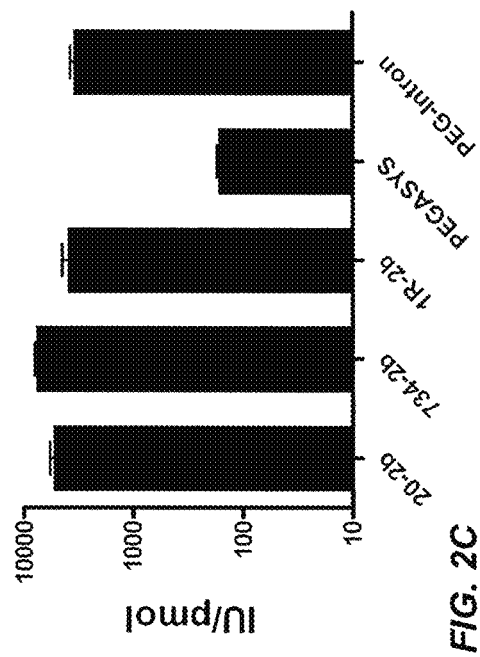
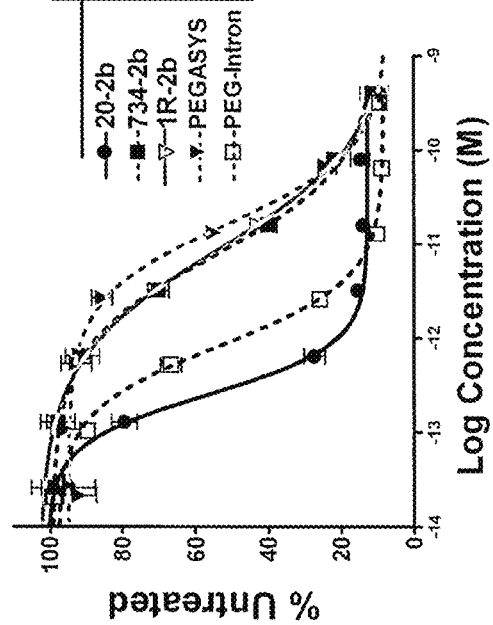
FIG. 2A  FIG. 2B  FIG. 2C  FIG. 2D

|  | hG-CSF standard | G-CSF-DDD2 | hA20-G-CSF lot101008 | h734-G-CSF lot103108 |
|---|---|---|---|---|
| EC50 (pM) | 5.447 | 3.141 | 0.3557 | 0.1566 |

TETRAMERIC CYTOKINES WITH IMPROVED BIOLOGICAL ACTIVITY

RELATED APPLICATIONS

This application is a divisional of U.S. patent application Ser. No. 14/067,296 (now U.S. Pat. No. 9,498,542), filed Oct. 30, 2013, which was a continuation of U.S. patent application Ser. No. 13/219,940 (now U.S. Pat. No. 8,597,659), filed Aug. 29, 2011, which was a divisional of U.S. patent application Ser. No. 12/752,649 (now U.S. Pat. No. 8,034,352), filed Apr. 1, 2010, which was a continuation-in-part of U.S. patent application Ser. No. 12/418,877 (now U.S. Pat. No. 7,906,118), filed Apr. 6, 2009, which claimed the benefit under 35 U.S.C. 119(e) of U.S. Provisional Patent Application Ser. No. 61/043,932, filed Apr. 10, 2008, 61/104,916, filed Oct. 13, 2008 and 61/119,542, filed Dec. 3, 2008, and which was a continuation-in-part of U.S. patent application Ser. No. 12/396,605 (now U.S. Pat. No. 7,858,070), filed Mar. 3, 2009 (which was a divisional of U.S. Pat. No. 7,527,787); U.S. Ser. No. 12/396,965 (now U.S. Pat. No. 7,871,622), filed Mar. 3, 2009 (which was a divisional of U.S. Pat. No. 7,521,056); U.S. Pat. Nos. 7,550,143 and 7,534,866; and U.S. Pat. No. 7,666,400. Those applications claimed the benefit under 35 U.S.C. 119(e) of U.S. Provisional Patent Application Ser. No. 60/668,603, filed Apr. 6, 2005; 60/751,196, filed Dec. 16, 2005, 60/782,332, filed Mar. 14, 2006; and 60/864,530, filed Nov. 6, 2006. This application claims the benefit under 35 U.S.C. 119(e) of U.S. Provisional Patent Application Ser. Nos. 61/168,657 and 61/168,668, filed Apr. 13, 2009. The entire text of each priority application is incorporated herein by reference.

SEQUENCE LISTING

The instant application contains a Sequence Listing which has been submitted via EFS-Web and is hereby incorporated by reference in its entirety. Said ASCII copy, created on Mar. 31, 2010, is named IBC124US.txt and is 13,788 bytes in size.

BACKGROUND

Field of the Invention

The present invention relates to the design and generation of multimeric cytokines that retain in vitro activity and show enhanced in vivo efficacy. In preferred embodiments, the dock-and-lock (DNL) method is used to produce tetrameric cytokines that are anchored on a humanized monoclonal antibody or fragment thereof (MAb) by site-specific conjugation of a cytokine-based DDD moiety with a recombinant IgG, in which each of the two antibody heavy chains is fused to an AD moiety and dimers of the DDD moiety bind to each AD moiety. In a more preferred embodiment, the cytokine is erythropoietin, granulocyte colony-stimulating factor (G-CSF) or interferon-α2b (IFNα2b), although the disclosed methods may be used to produce DNL constructs comprising any tetrameric cytokine and antibody or fragment. In a most preferred embodiment, a humanized anti-CD20 MAb (hA20) is conjugated to IFNα2b to form a 20-2b DNL construct that comprises four copies of IFNα2b. The cytokine-MAb constructs are of use to treat a variety of disease states and show greater potency against target cells, such as tumors, than the parent MAb alone, the cytokine alone, a non-conjugated combination of MAb and cytokine or cytokine conjugated to a control MAb.

Related Art

IFNα2b

Interferon-α (IFNα) has been reported to have anti-tumor activity in both animal models of cancer (Ferrantini et al., 1994, J Immunol 153:4604-15) and human cancer patients (Gutterman et al., 1980, Ann Intern Med 93:399-406). IFNα can exert a variety of direct anti-tumor effects, including down-regulation of oncogenes, up-regulation of tumor suppressors, enhancement of immune recognition via increased expression of tumor surface MEW class I proteins, potentiation of apoptosis, and sensitization to chemotherapeutic agents (Gutterman et al., 1994, PNAS USA 91:1198-205; Matarrese et al., 2002, Am J Pathol 160:1507-20; Mecchia et al., 2000, Gene Ther 7:167-79; Sabaawy et al., 1999, Int J Oncol 14:1143-51; Takaoka et al, 2003, Nature 424:516-23). For some tumors, IFNα can have a direct and potent anti-proliferative effect through activation of STAT1 (Grimley et al., 1998 Blood 91:3017-27). Indirectly, IFNα can inhibit angiogenesis (Sidky and Borden, 1987, Cancer Res 47:5155-61) and stimulate host immune cells, which may be vital to the overall antitumor response but has been largely under-appreciated (Belardelli et al., 1996, Immunol Today 17:369-72). IFNα has a pleiotropic influence on immune responses through effects on myeloid cells (Raefsky et al, 1985, J Immunol 135:2507-12; Luft et al, 1998, J Immunol 161:1947-53), T-cells (Carrero et al, 2006, J Exp Med 203:933-40; Pilling et al., 1999, Eur J Immuol 29:1041-50), and B-cells (Le et al, 2001, Immunity 14:461-70). As an important modulator of the innate immune system, IFNα induces the rapid differentiation and activation of dendritic cells (Belardelli et al, 2004, Cancer Res 64:6827-30; Paquette et al., 1998, J Leukoc biol 64:358-67; Santini et al., 2000, J Exp med 191:1777-88) and enhances the cytotoxicity, migration, cytokine production and antibody-dependent cellular cytotoxicity (ADCC) of NK cells (Biron et al., 1999, Annu Rev Immunol 17:189-220; Brunda et al. 1984, Cancer Res 44:597-601).

The promise of IFNα as a cancer therapeutic has been hindered primarily due to its short circulating half-life and systemic toxicity. PEGylated forms of IFNα2 display increased circulation time, which augments their biological efficacy (Harris and Chess, 2003, Nat Rev Drug Discov 2:214-21; Osborn et al., 2002, J Pharmacol Exp Ther 303: 540-8). Fusion of IFNα to a monoclonal antibody (MAb) can provide similar benefits as PEGylation, including reduced renal clearance, improved solubility and stability, and markedly increased circulating half-life. The immediate clinical benefit of this is the requirement for less frequent and lower doses, allowing prolonged therapeutic concentrations. Targeting of IFNα to tumors using MAbs to a tumor-associated antigen (TAA) can significantly increase its tumor accretion and retention while limiting its systemic concentration, thereby increasing the therapeutic index. Increased tumor concentrations of IFNα can augment its direct antiproliferative, apoptotic and anti-angiogenic activity, as well as prime and focus an antitumor immune response. Studies in mice using syngeneic murine IFNα-secreting transgenic tumors demonstrated an enhanced immune response elicited by a localized concentration of IFNα (Ferrantini et al., 2007, Biochimie 89:884-93).

G-CSF

Granulocyte colony-stimulating factor (G-CSF) stimulates the production of neutrophils and regulates the survival, proliferation, and differentiation of hematopoietic progenitors. In the U.S., a recombinant methionyl human G-CSF and its longer-acting PEGylated form are used primarily for treating chemotherapy-induced neutropenia to directly increase neutrophil counts and for mobilizing transplantable stem cells from bone marrow to the blood for easier collection and processing.

Erythropoietin

Erythropoietin (Epo) is a hematopoietic growth factor that stimulates the proliferation and differentiation of erythrocytes into mature red blood cells. Several recombinant human Epo are currently used for the treatment of anemia, predominantly associated with chronic renal failure and post cancer chemotherapy. However, the short half-life (4-13 hours) of rhEpo necessitates frequent dosing and, therefore, increasing the serum half-life of Epo to allow less frequent dosing is highly desirable and has been an important goal for developing next-generation Epo.

Each of the cytokines discussed above, as well as many other cytokines, would benefit from methods and compositions to provide prolonged bioavailability and/or targeting of cytokine to specific cell types, according to the methods and compositions of the instant invention.

SUMMARY OF THE INVENTION

The present invention discloses methods and compositions for conjugates of cytokines and antibodies, prepared using the Dock-and-Lock (DNL) method (Chang et al., 2007, Clin Cancer Res 13:5586s-91s), which generates stable and defined conjugates suitable for in vivo applications. In preferred embodiments, the DNL complexes comprise four copies of a cytokine, such as IFNα2b, G-CSF or Epo, each attached to a dimerization and docking domain (DDD) moiety. The DDD moieties spontaneously dimerize and each DDD dimer binds to an anchor domain (AD moiety). In more preferred embodiments, an AD moiety is attached to the C-terminal end of each heavy chain constant region of an IgG antibody, resulting in a tetrameric cytokine-IgG DNL complex.

However, the skilled artisan will realize that other types of DNL complexes with different structures and different ratios of cytokine to antibody or antibody fragment may be constructed and used within the scope of the claimed methods and compositions, such as those disclosed in U.S. Pat. Nos. 7,550,143; 7,521,056; 7,534,866; 7,527,787 and 7,666,400, the Examples section of each of which is incorporated herein by reference. For convenience, the DNL constructs of interest are generally referred to herein as cytokine-MAb constructs. However, the skilled artisan will realize that the designation "MAb" is used as a generic term to indicate the presence of an antibody or antigen-binding fragment thereof.

The skilled artisan will further realize that any known antibody or antigen-binding fragment thereof may be incorporated into the cytokine-MAb DNL constructs. In certain embodiments, the complex is of use for cancer therapy and the antibody binds to a tumor associated antigen (TAA). A variety of tumor-associated antigens are known in the art, including but not limited to carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM-6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, and an oncogene product.

Exemplary anti-cancer antibodies that may be utilized in the cytokine-MAb DNL constructs include, but are not limited to, hR1 (anti-IGF-1R, U.S. patent application Ser. No. 12/722,645, filed Mar. 12, 2010) hPAM4 (anti-mucin, U.S. Pat. No. 7,282,567), hA20 (anti-CD20, U.S. Pat. No. 7,151,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 5,789,554), hMu-9 (anti-CSAp, U.S. Pat. No. 7,387,772), hL243 (anti-HLA-DR, U.S. Pat. No. 7,612,180), hMN-14 (anti-CEA, U.S. Pat. No. 6,676,924), hMN-15 (anti-CEA, U.S. Pat. No. 8,287,865), hRS7 (anti-EGP-1, U.S. Pat. No. 7,238,785) and hMN-3 (anti-CEA, U.S. Pat. No. 7,541,440) the Examples section of each cited patent or application incorporated herein by reference. The skilled artisan will realize that this list is not limiting and any other known anti-TAA antibody may be incorporated into the cytokine-MAb DNL constructs.

In certain preferred embodiments, the target antigen may be CD20, which is an attractive candidate TAA for the therapy of B-cell lymphomas and other hematopoietic disorders. Anti-CD20 immunotherapy with rituximab is one of the most successful therapies against lymphoma, with relatively low toxicity (McLaughlin et al., 1998, J Clin Oncol 16:2825-33). Since rituximab is a chimeric antibody that can show immunogenicity in some patient populations and has considerably long infusion times for the initial administration (Cheson et al., 2008, NEJM 359:613-26), a better candidate for CD20-targeting is the humanized MAb, veltuzumab (Stein et al., 2004, Clin Cancer Res 10:2868-78). Combination therapies with rituximab and IFNα currently under clinical evaluation have shown improved efficacy over rituximab alone (Kimby et al., 2008, Leuk Lymphoma 49:102-12; Salles et al., 2008, Blood 112:4824-31). These studies demonstrate some advantages of this combination as well as the drawbacks associated with IFNα. In addition to weekly infusions with rituximab, patients are typically administered IFNα three times/week for months and suffer the flu-like symptoms that are common side effects associated with IFNα therapy and which limit the tolerable dose. An anti-CD20 MAb-IFNα conjugate could allow the less frequent administration of a single agent at a lower dose, limit or eliminate side effects, and may result in far superior efficacy.

Other types of target antigen are of use for antibody-based therapy of different disease states and cytokine-MAb DNL constructs incorporating antibodies that target any such alternative antigen may be utilized in the claimed methods and compositions.

Exemplary cytokines that may be incorporated into the cytokine-MAb DNL constructs include but are not limited to MIF (macrophage migration inhibitory factor), HMGB-1 (high mobility group box protein 1), TNF-α, IL-1, IL-2, IL-3, IL-4, IL-5, IL-6, IL-7, IL-8, IL-9, IL-10, IL-11, IL-12, IL-13, IL-15, IL-16, IL-17, IL-18, IL-19, IL-23, IL-24, CCL19, CCL21, IL-8, MCP-1, RANTES, MIP-1A, MIP-1B, ENA-78, MCP-1, IP-10, Gro-β, Eotaxin, interferon-α, -β, -λ, G-CSF, GM-CSF, SCF, PDGF, MSF, Flt-3 ligand, erythropoietin, thrombopoietin, CNTF, leptin, oncostatin M, VEGF, EGF, FGF, PlGF, insulin, hGH, calcitonin, Factor VIII, IGF, somatostatin, tissue plasminogen activator and LIF. As discussed below, the amino acid sequences of a wide variety of human cytokines are known in the art and may be obtained, for example, from the NCBI protein sequence database and other publicly known sources.

Certain embodiments may concern therapeutic or diagnostic conjugates of cytokine-MAb DNL constructs, bound to at least one therapeutic agent or at least one diagnostic agent. Constructs with multiple therapeutic agents of the same or different type are also encompassed. Alternatively, the cytokine-MAb DNL constructs may be administered in combination with at least one therapeutic agent administered before, simultaneously with or after the cytokine-MAb construct. Any therapeutic agent known in the art, as discussed in more detail below, may be utilized in combination with or attached to cytokine-MAb DNL construct, including but not limited to radionuclides, immunomodulators, anti-angiogenic agents, cytokines, chemokines, growth factors, hormones, drugs, prodrugs, enzymes, oligonucleotides, siRNAs, pro-apoptotic agents, photoactive therapeutic agents, cytotoxic agents, chemotherapeutic agents, toxins, other antibodies or antigen binding fragments thereof.

The cytokine-MAb complexes are of use for therapy of a wide variety of diseases or medical conditions, including but not limited to cancer, autoimmune disease, hyperplasia, septicemia, diabetes, inflammatory bowel disease, Crohn's disease, ulcerative colitis, rheumatoid arthritis, sarcoidosis, asthma, anemia, neutropenia and Osler-Webber Syndrome.

In particular embodiments, the disclosed methods and compositions may be of use to treat autoimmune disease, such as acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, juvenile diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

Exemplary types of cancers that may be treated with the cytokine-MAb DNL constructs include but are not limited to acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal cancer, gastric cancer, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, urinary bladder cancer, Wilms' tumor, Ewing sarcoma, neuroendocrine tumors, glioblastomas, neuroblastoma, melanoma, skin cancer, liver cancer, medullary thyroid carcinoma.

Still other embodiments relate to DNA sequences encoding fusion proteins, such as cytokine-DDD fusion proteins or Fab-AD fusion proteins, vectors and host cells containing the DNA sequences, and methods of making the cytokine-MAb DNL constructs.

A particularly preferred embodiment concerns 20-2b, an IFNα-MAb DNL construct comprising four IFNα2b groups attached to a humanized anti-CD20 antibody (hA20). The 20-2b construct was found to be a superior anti-lymphoma agent to either the parent antibody alone, the IFNα cytokine alone, or a non-targeting IFNα-MAb by in vitro proliferation, ex vivo lymphoma cell depletion, and in vivo therapy studies. The 20-2b construct is of particular use for therapy of lymphomas, leukemias, myelomas and related conditions.

DETAILED DESCRIPTION OF THE INVENTION

Definitions

As used herein, the terms "a", "an" and "the" may refer to either the singular or plural, unless the context otherwise makes clear that only the singular is meant.

As used herein, the term "about" means plus or minus ten percent (10%) of a value. For example, "about 100" would refer to any number between 90 and 110.

An antibody refers to a full-length (i.e., naturally occurring or formed by normal immunoglobulin gene fragment recombinatorial processes) immunoglobulin molecule (e.g., an IgG antibody) or an immunologically active, antigen-binding portion of an immunoglobulin molecule, like an antibody fragment.

An antibody fragment is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" also includes isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). As used herein, the term "antibody fragment" does not include portions of antibodies without antigen binding activity, such as Fc fragments or single amino acid residues.

The term antibody fusion protein may refer to a recombinantly produced antigen-binding molecule in which one or more of the same or different single-chain antibody or antibody fragment segments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only bind with one epitope. The fusion protein may comprise a single antibody component, a multivalent or multispecific combination of different antibody components or multiple copies of the same antibody component. The fusion protein may additionally comprise an antibody or an antibody fragment and a therapeutic agent, such as a cytokine. Other examples of therapeutic agents suitable for such fusion proteins include immunomodulators and toxins. One preferred toxin comprises a ribonuclease (RNase), preferably a recombinant RNase. However, the term is not limiting and a variety of protein or peptide effectors may be incorporated into a fusion protein. In another non-limiting example, a fusion protein may comprise an AD or DDD sequence for producing a DNL construct as discussed below.

BRIEF DESCRIPTION OF THE DRAWINGS

FIG. 1A is a diagrammatic illustration of the gene and protein structures for antibody-AD2 DNL subunits.

FIG. 1B is a diagrammatic illustration of the gene and protein structures for interferon-α2b-DDD2 DNL subunits.

FIG. 1C is a diagrammatic illustration of the protein structures for antibody-interferon-α2b DNL complexes in which the subunits are attached by AD-DDD binding interactions.

FIG. 2A shows in vitro IFNα activity in a cytokine-MAb DNL construct compared to PEGylated or native IFNα, using a cell-based reporter gene assay. Specific activities (IU/pmol) measured as described in the Examples. The activity of known concentrations of each test article was extrapolated from a rhIFNα2b standard curve. Cultures were grown in the presence of increasing concentrations of 20-2b (●), 734-2b (■), v-mab (0), v-mab+734-2b (□), PEGASYS® (▼), PEG-INTRON® (▲) or 1R-2b (∇) and the relative viable cell densities were measured with MTS. The % of the signal obtained from untreated cells was plotted vs. the log of the molar concentration. Dose-response curves and $EC_{50}$ values were generated using Prism software. Error bars, SD.

FIG. 2B shows in vitro IFNα activity in a cytokine-MAb DNL construct compared to PEGylated or native IFNα, using a viral protection assay with EMC virus and A549 cells. Specific activities (IU/pmol) measured as described in the Examples. The activity of known concentrations of each test article was extrapolated from a rhIFNα2b standard curve. Cultures were grown in the presence of increasing concentrations of 20-2b (●), 734-2b (■), v-mab (○), v-mab+734-2b (□), PEGASYS® (▼), PEG-INTRON® (▲) or 1R-2b (∇) and the relative viable cell densities were measured with MTS. The % of the signal obtained from untreated cells was plotted vs. the log of the molar concentration. Dose-response curves and $EC_{50}$ values were generated using Prism software. Error bars, SD.

FIG. 2C shows in vitro IFNα activity in a cytokine-MAb DNL construct compared to PEGylated or native IFNα, using a lymphoma proliferation assays using Daudi cells. Specific activities (IU/pmol) measured as described in the Examples. The activity of known concentrations of each test article was extrapolated from a rhIFNα2b standard curve. Cultures were grown in the presence of increasing concentrations of 20-2b (●), 734-2b (■), v-mab (○), v-mab+734-2b (□), PEGASYS® (▼), PEG-INTRON® (▲) or 1R-2b (∇) and the relative viable cell densities were measured with MTS. The % of the signal obtained from untreated cells was plotted vs. the log of the molar concentration. Dose-response curves and $EC_{50}$ values were generated using Prism software. Error bars, SD.

FIG. 2D shows in vitro IFNα activity in a cytokine-MAb DNL construct compared to PEGylated or native IFNα, using a lymphoma proliferation assays using Jeko-1 cells. Specific activities (IU/pmol) measured as described in the Examples. The activity of known concentrations of each test article was extrapolated from a rhIFNα2b standard curve. Cultures were grown in the presence of increasing concentrations of 20-2b (●), 734-2b (■), v-mab (○), v-mab+734-2b (□), PEGASYS® (▼), PEG-INTRON® (▲) or 1R-2b (∇) and the relative viable cell densities were measured with MTS. The % of the signal obtained from untreated cells was plotted vs. the log of the molar concentration. Dose-response curves and $EC_{50}$ values were generated using Prism software. Error bars, SD.

DOCK AND LOCK (DNL) METHOD

Figure 3:
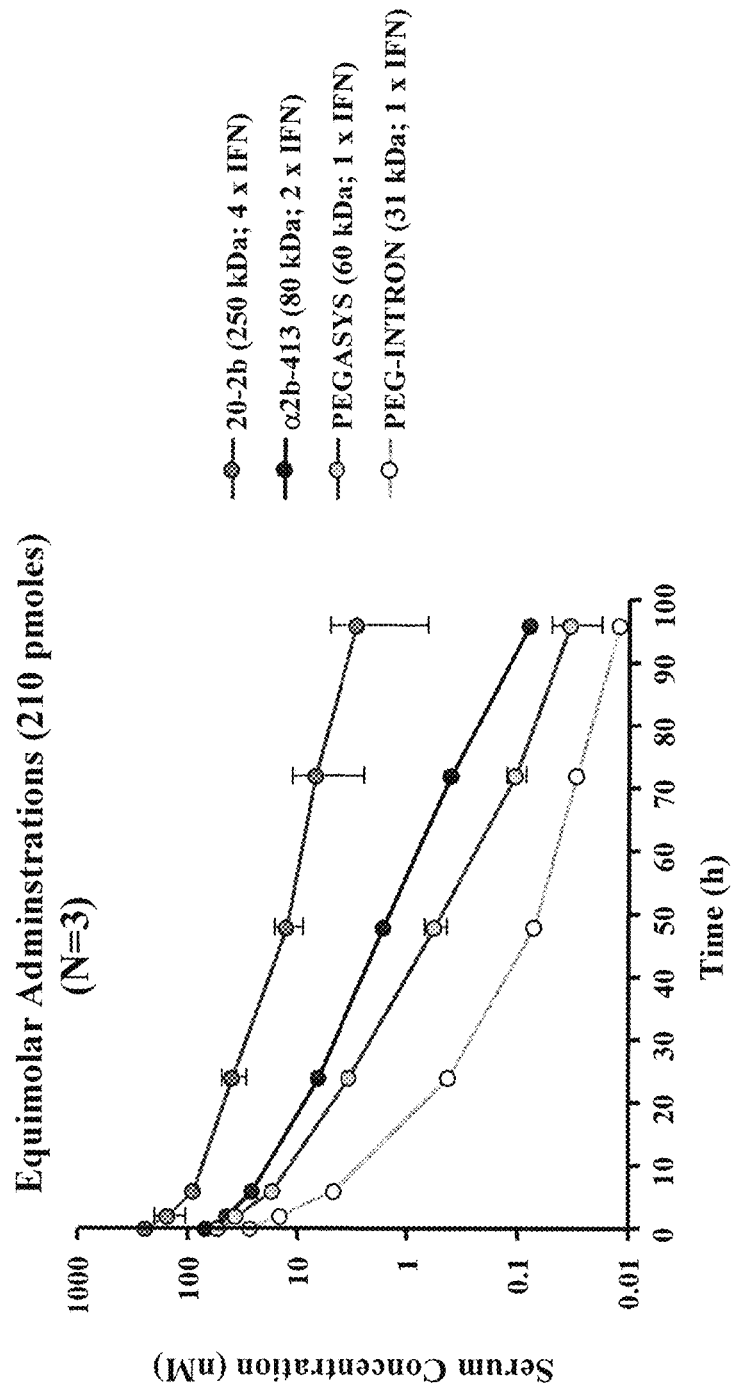
FIG. 3 shows the results of pharmacokinetic analyses in Swiss-Webster mice. Mice were administered 20-2b, α2b-413, PEGINTRON® or PEGASYS® and serum samples were analyzed for IFNα2b concentration by ELISA over 96 hours. Serum elimination curves are shown. Serum half-life ($T_{1/2}$) elimination rates and mean residence times (MRT) are summarized in the inserted table.

The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RH), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RH dimers ranging from 2 to 90 nM (Alto et al., Proc. Natl. Acad. Sci. USA. 2003; 100:4445). Interestingly, AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

DDD of Human RIIα and AD of AKAPs as Linker Modules

We have developed a platform technology to utilize the DDD of human RIIα and the AD of AKAP proteins as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically.

In preferred embodiments, the cytokine-MAb DNL constructs are based on a variation of the $a_2b$ structure, in which an IgG immunoglobulin molecule is attached at its C-terminal end to two copies of an AD moiety. Each AD moiety is capable of binding to two DDD moieties in the form of a dimer. By attaching a cytokine to each DDD moiety, four copies of cytokine are conjugated to each IgG molecule. In more preferred embodiments, each of the four cytokines in a DNL construct is identical.

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances. The DNL method was disclosed in U.S. Pat. Nos. 7,550,143; 7,521,056; 7,534,866; 7,527, 787 and 7,666,400.

In preferred embodiments, as illustrated in the Examples below, the effector moiety is a protein or peptide, more preferably an antibody, antibody fragment or cytokine, which can be linked to a DDD or AD unit to form a fusion protein or peptide. A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

DDD and AD Sequence Variants

In certain embodiments, the AD and DDD sequences incorporated into the cytokine-PEG DNL complex comprise the amino acid sequences of DDD1 (SEQ ID NO:1) and AD1 (SEQ ID NO:3) below. In more preferred embodiments, the AD and DDD sequences comprise the amino acid sequences of DDD2 (SEQ ID NO:2) and AD2 (SEQ ID NO:4), which are designed to promote disulfide bond formation between the DDD and AD moieties.

```
DDD1
                                          (SEQ ID NO: 1)
SHIQIPPGLTELLQGYTVEVLRQQPPDLVEFAVEYFTRLREARA

DDD2
                                          (SEQ ID NO: 2)
CGHIQIPPGLTELLQGYTVEVLRQQPPDLVEFAVEYFTRLREARA

AD1
                                          (SEQ ID NO: 3)
QIEYLAKQIVDNAIQQA

AD2
                                          (SEQ ID NO: 4)
CGQIEYLAKQIVDNAIQQAGC
```

However, in alternative embodiments sequence variants AD and/or DDD moieties may be utilized in construction of the cytokine-PEG DNL complexes. The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined below in SEQ ID NO:1. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding. Thus, a potential alternative DDD sequence of use for construction of DNL complexes is shown in SEQ ID NO:5, wherein "X" represents a conservative amino acid substitution. Conservative amino acid substitutions are discussed in more detail below, but could involve for example substitution of an aspartate residue for a glutamate residue, or a leucine or valine residue for an isoleucine residue, etc. Such conservative amino acid substitutions are well known in the art.

```
Human DDD sequence from protein kinase A
                                          (SEQ ID NO: 1)
SHIQIPPGLTELLQGYTVEVLRQQPPDLVEFAVEYFTRLREARA (SEQ ID NO: 5)
XXIXIXXXLXXLLXXYXVXVLXXXXXXLVXFXVXYFXXLXXXXX
```

Alto et al. (2003) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3. Therefore, the skilled artisan will realize that variants which may function for DNL constructs are indicated by SEQ ID NO:6, where "X" is a conservative amino acid substitution.

```
AKAP-IS sequence
                                          (SEQ ID NO: 3)
QIEYLAKQIVDNAIQQA (SEQ ID NO: 6)
XXXXXAXXIVXXAIXXX
```

Similarly, Gold (2006) utilized crystallography and peptide screening to develop a SuperAKAP-IS sequence (SEQ ID NO:7), exhibiting a five order of magnitude higher selectivity for the RII isoform of PKA compared with the RI isoform. Underlined residues indicate the positions of amino acid substitutions, relative to the AKAP-IS sequence, that increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare cytokine-PEG DNL constructs. Other alternative sequences that might be substituted for the AKAP-IS AD sequence are shown in SEQ ID NO:8-10. Substitutions relative to the AKAP-IS sequence are underlined. It is anticipated that, as with the AKAP-IS sequence shown in SEQ ID NO:3, the AD moiety may also include the additional N-terminal residues cysteine and glycine and C-terminal residues glycine and cysteine, as shown in SEQ ID NO:4.

```
SuperAKAP-IS
                                          (SEQ ID NO: 7)
QIEYVAKQIVDYAIHQA Alternative AKAP sequences
                                          (SEQ ID NO: 8)
QIEYKAKQIVDHAIHQA (SEQ ID NO: 9)
QIEYHAKQIVDHAIHQA (SEQ ID NO: 10)
QIEYVAKQIVDHAIHQA
```

Stokka et al. (2006) also developed peptide competitors of AKAP binding to PKA, shown in SEQ ID NO:11-13. The peptide antagonists were designated as Ht31 (SEQ ID NO:11), RIAD (SEQ ID NO:12) and PV-38 (SEQ ID NO:13). The Ht-31 peptide exhibited a greater affinity for the RII isoform of PKA, while the RIAD and PV-38 showed higher affinity for RI.

```
Ht31
                                              (SEQ ID NO: 11)
DLIEEAASRIVDAVIEQVKAAGAY

RIAD
                                              (SEQ ID NO: 12)
LEQYANQLADQIIKEATE

PV-38
                                              (SEQ ID NO: 13)
FEELAWKIAKMIWSDVFQQC
```

Hundsrucker et al. (2006) developed still other peptide competitors for AKAP binding to PKA, with a binding constant as low as 0.4 nM to the DDD of the RII form of PKA. The sequences of various AKAP antagonistic peptides is provided in Table 1 of Hundsrucker et al. (incorporated herein by reference). Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence are shown in SEQ ID NO:14-16.

```
AKAP-IS
                                              (SEQ ID NO: 3)
QIEYLAKQIVDNAIQQA

AKAP7δ-wt-pep
                                              (SEQ ID NO: 14)
PEDAELVRLSKRLVENAVLKAVQQY AKAP7δ-L304T-pep
                                              (SEQ ID NO: 15)
PEDAELVRTSKRLVENAVLKAVQQY AKAP7δ-L308D-pep
                                              (SEQ ID NO: 16)
PEDAELVRLSKRDVENAVLKAVQQY
```

Can et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:2. Residues that were particularly conserved are further indicated by italics. The residues overlap with, but are not identical to those suggested by Kinderman et al. (2006) to be important for binding to AKAP proteins. Thus, a potential DDD sequence is indicated in SEQ ID NO:17, wherein "X" represents a conservative amino acid substitution.

```
                                              (SEQ ID NO: 1)
SHIQIPPGLTELLQGYTVEVLRQQPPDLVEFAVEYFTRLREARA (SEQ ID NO: 17)
XHIXIPXGLXELLQGYTXEVLRXQPXDLVEFAXXYFXXLXEXRX
```

The skilled artisan will realize that in general, those amino acid residues that are highly conserved in the DDD and AD sequences from different proteins are ones that it may be preferred to remain constant in making amino acid substitutions, while residues that are less highly conserved may be more easily varied to produce sequence variants of the AD and/or DDD sequences described herein.

In addition to sequence variants of the DDD and/or AD moieties, in certain embodiments it may be preferred to introduce sequence variations in the antibody moiety or the linker peptide sequence joining the antibody with the AD sequence. In one illustrative example, three possible variants of fusion protein sequences, are shown in SEQ ID NO:18-20.

```
(L)
                                              (SEQ ID NO: 18)
QKSLSLSPGLGSGGGGSGGCG (A)
                                              (SEQ ID NO: 19)
QKSLSLSPGAGSGGGGSGGCG (-)
                                              (SEQ ID NO: 20)
QKSLSLSPGGSGGGGSGGCG
```

Cytokines and Other Immunomodulators

In certain preferred embodiments, the effector moiety is an immunomodulator. An immunomodulator is an agent that when present, alters, suppresses or stimulates the body's immune system. Immunomodulators of use may include a cytokine, a stem cell growth factor, a lymphotoxin, an hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "Si factor".

In more preferred embodiments, the effector moieties are cytokines, such as lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); placenta growth factor (PlGF), hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor (TNF, such as TNF-α) and LT.

The amino acid sequences of protein or peptide immunomodulators, such as cytokines, are well known in the art and any such known sequences may be used in the practice of the instant invention. The skilled artisan is aware of numerous sources of public information on cytokine sequence. For example, the NCBI database contains both protein and encoding nucleic acid sequences for a large number of cytokines and immunomodulators, such as erythropoietin (GenBank NM 000799), IL-1 beta (GenPept AAH08678), GM-CSF (GenPept AAA52578), G-CSF (GenPept CAA27290), TNF-α (GenPept CAA26669), interferon-alpha (GenPept AAA52716.1), interferon-alpha 2b (GenPept AAP20099.1) and virtually any of the peptide or protein immunomodulators listed above. It is a matter of routine for the skilled artisan to identify an appropriate amino acid and/or nucleic acid sequence for essentially any protein or peptide effector moiety of interest.

Antibodies and Antibody Fragments

In various embodiments, antibodies or antigen-binding fragments of antibodies may be attached to the multimeric cytokines. Antigen-binding antibody fragments are well known in the art, such as $F(ab')_2$, $F(ab)_2$, Fab', Fab, Fv, scFv and the like, and any such known fragment may be used. As used herein, an antigen-binding antibody fragment refers to any fragment of an antibody that binds with the same antigen that is recognized by the intact or parent antibody. Techniques for preparing AD and/or DDD conjugates of virtually any antibody or fragment of interest are known (e.g., U.S. Pat. Nos. 7,550,143; 7,521,056; 7,534,866; 7,527,787 and 7,666,400).

An antibody or fragment thereof may be used which is not conjugated to a therapeutic agent—referred to as a "naked" antibody or fragment thereof. In alternative embodiments, antibodies or fragments may be conjugated to one or more therapeutic and/or diagnostic agents. A wide variety of such therapeutic and diagnostic agents are known in the art, as discussed in more detail below, and any such known therapeutic or diagnostic agent may be used.

Techniques for preparing monoclonal antibodies against virtually any target antigen are well known in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. The use of antibody components derived from humanized, chimeric or human antibodies obviates potential problems associated with the immunogenicity of murine constant regions.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat'l Acad. Sci. USA* 86: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Generally, those human FR amino acid residues that differ from their murine counterparts and are located close to or touching one or more CDR amino acid residues would be candidates for substitution.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the µ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art (see, e.g., Pasqualini and Ruoslahti, 1996, Nature 380:364-366; Pasqualini, 1999, The Quart. J. Nucl. Med. 43:159-162).

Phage display can be performed in a variety of formats, for their review, see e.g. Johnson and Chiswell, *Current Opinion in Structural Biology* 3:5564-571 (1993). Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Fragments

Antibody fragments which recognize specific epitopes can be generated by known techniques. Antibody fragments are antigen binding portions of an antibody, such as F(ab')$_2$, Fab', F(ab)$_2$, Fab, Fv, sFv and the like. F(ab')$_2$ fragments can be produced by pepsin digestion of the antibody molecule and Fab' fragments can be generated by reducing disulfide bridges of the F(ab')$_2$ fragments. Alternatively, Fab' expression libraries can be constructed (Huse et al., 1989, *Science*, 246:1274-1281) to allow rapid and easy identification of monoclonal Fab' fragments with the desired specificity. F(ab)$_2$ fragments may be generated by papain digestion of an antibody and Fab fragments obtained by disulfide reduction.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are described in U.S. Pat. No. 4,704,692, U.S. Pat. No. 4,946,778, R. Raag and M. Whitlow, "*Single Chain Fvs.*" FASEB Vol 9:73-80 (1995) and R. E. Bird and B. W. Walker, "*Single Chain Antibody Variable Regions,*" TIBTECH, Vol 9: 132-137 (1991).

Techniques for producing single domain antibodies (DABs) are also known in the art, as disclosed for example in Cossins et al. (2006, Prot Express Purif 51:253-259), incorporated herein by reference.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. These methods are described, for example, by Goldenberg, U.S. Pat. Nos. 4,036,945 and 4,331,647 and references contained therein. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Known Antibodies

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312, 318; 7,282,567; 7,151,164; 7,074,403; 7,060,802; 7,056, 509; 7,049,060; 7,045,132; 7,041,803; 7,041,802; 7,041, 293; 7,038,018; 7,037,498; 7,012,133; 7,001,598; 6,998, 468; 6,994,976; 6,994,852; 6,989,241; 6,974,863; 6,965, 018; 6,964,854; 6,962,981; 6,962,813; 6,956,107; 6,951, 924; 6,949,244; 6,946,129; 6,943,020; 6,939,547; 6,921, 645; 6,921,645; 6,921,533; 6,919,433; 6,919,078; 6,916, 475; 6,905,681; 6,899,879; 6,893,625; 6,887,468; 6,887, 466; 6,884,594; 6,881,405; 6,878,812; 6,875,580; 6,872, 568; 6,867,006; 6,864,062; 6,861,511; 6,861,227; 6,861, 226; 6,838,282; 6,835,549; 6,835,370; 6,824,780; 6,824, 778; 6,812,206; 6,793,924; 6,783,758; 6,770,450; 6,767, 711; 6,764,688; 6,764,681; 6,764,679; 6,743,898; 6,733, 981; 6,730,307; 6,720,155; 6,716,966; 6,709,653; 6,693, 176; 6,692,908; 6,689,607; 6,689,362; 6,689,355; 6,682, 737; 6,682,736; 6,682,734; 6,673,344; 6,653,104; 6,652, 852; 6,635,482; 6,630,144; 6,610,833; 6,610,294; 6,605, 441; 6,605,279; 6,596,852; 6,592,868; 6,576,745; 6,572, 856; 6,566,076; 6,562,618; 6,545,130; 6,544,749; 6,534, 058; 6,528,625; 6,528,269; 6,521,227; 6,518,404; 6,511, 665; 6,491,915; 6,488,930; 6,482,598; 6,482,408; 6,479, 247; 6,468,531; 6,468,529; 6,465,173; 6,461,823; 6,458, 356; 6,455,044; 6,455,040; 6,451,310; 6,444,206' 6,441, 143; 6,432,404; 6,432,402; 6,419,928; 6,413,726; 6,406, 694; 6,403,770; 6,403,091; 6,395,276; 6,395,274; 6,387, 350; 6,383,759; 6,383,484; 6,376,654; 6,372,215; 6,359, 126; 6,355,481; 6,355,444; 6,355,245; 6,355,244; 6,346, 246; 6,344,198; 6,340,571; 6,340,459; 6,331,175; 6,306, 393; 6,254,868; 6,187,287; 6,183,744; 6,129,914; 6,120, 767; 6,096,289; 6,077,499; 5,922,302; 5,874,540; 5,814, 440; 5,798,229; 5,789,554; 5,776,456; 5,736,119; 5,716, 595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Amino Acid Substitutions

In certain embodiments, the disclosed methods and compositions may involve production and use of proteins or peptides with one or more substituted amino acid residues. As discussed above, methods for making monoclonal antibodies against virtually any target antigen are well known in the art. Typically, these result in production of murine antibodies against a target antigen. As is well known in the art, the antigen-binding specificity of murine monoclonal antibodies is determined largely by the hypervariable complementarity determining region (CDR) sequences. Murine antibodies generally comprise 6 CDR sequences, 3 on the antibody light chain and 3 on the heavy chain. As described in detail above, chimeric, humanized or human versions of murine antibodies may be constructed by techniques such as CDR grafting, where the murine CDR sequences are inserted into, for example, human antibody framework and constant region sequences, or by attaching the entire murine variable region sequences to human antibody constant region sequences. In alternative embodiments, the variable region sequences of an antibody may be constructed, for example, by chemical synthesis and assembly of oligonucleotides encoding the entire light and heavy chain variable regions of an antibody.

In various embodiments, the structural, physical and/or therapeutic characteristics of native, chimeric, humanized or human antibodies, cytokines, or AD or DDD sequences may be optimized by replacing one or more amino acid residues. For example, it is well known in the art that the functional characteristics of humanized antibodies may be improved by substituting a limited number of human framework region (FR) amino acids with the corresponding FR amino acids of the parent murine antibody. This is particularly true when the framework region amino acid residues are in close proximity to the CDR residues.

In other cases, the therapeutic properties of an antibody, such as binding affinity for the target antigen, the dissociation- or off-rate of the antibody from its target antigen, or even the effectiveness of induction of CDC (complement-dependent cytotoxicity) or ADCC (antibody dependent cellular cytotoxicity) by the antibody, may be optimized by a limited number of amino acid substitutions.

In alternative embodiments, the DDD and/or AD sequences used to make the cytokine-MAb DNL constructs may be further optimized, for example to increase the DDD-AD binding affinity. Potential sequence variations in DDD or AD sequences are discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Therapeutic Agents

In alternative embodiments, therapeutic agents such as cytotoxic agents, anti-angiogenic agents, pro-apoptotic agents, antibiotics, hormones, hormone antagonists, chemokines, drugs, prodrugs, toxins, enzymes or other agents may be used as adjunct therapies to the multimeric cytokines described herein. Drugs of use may possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use may include 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosurea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and *vinca* alkaloids.

Toxins of use may include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Chemokines of use may include RANTES, MCAF, MIP1-alpha, MIP1-Beta and IP-10.

In certain embodiments, anti-angiogenic agents, such as angiostatin, baculostatin, canstatin, maspin, anti-VEGF antibodies, anti-PlGF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide (roquinimex), thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Other useful therapeutic agents may comprise oligonucleotides, especially antisense oligonucleotides that preferably are directed against oncogenes and oncogene products, such as bcl-2 or p53. A preferred form of therapeutic oligonucleotide is siRNA.

Diagnostic Agents

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Immunoconjugates

In certain embodiments, the antibody component of the cytokine-MAb DNL construct may be conjugated to one or more therapeutic or diagnostic agents. The therapeutic agents do not need to be the same but can be different, e.g. a drug and a radioisotope. For example, $^{131}$I can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., *Int. J. Can-* cer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, incorporated herein in their entirety by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, incorporated herein by reference in their entirety. The engineered carbohydrate moiety is used to attach the therapeutic or diagnostic agent.

In some embodiments, a chelating agent may be attached to an antibody, antibody fragment or fusion protein and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. patent application Ser. No. 12/112,289, incorporated herein by reference in its entirety).

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates may be directly linked to antibodies or peptides, for example as disclosed in U.S. Pat. No. 4,824,659, incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br for radioimaging. The same chelates, when complexed with non-radioactive metals, such as manganese, iron and gadolinium are useful for MM. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F-Al conjugate may be complexed with chelating groups, such as DOTA, NOTA or NETA that are attached directly to antibodies or used to label targetable constructs in pre-targeting methods. Such F-18 labeling techniques are disclosed in U.S. patent application Ser. No. 12/112,289, filed Apr. 30, 2008, the entire text of which is incorporated herein by reference.

Methods of Therapeutic Treatment

Various embodiments concern methods of treating a cancer in a subject, such as a mammal, including humans, domestic or companion pets, such as dogs and cats, comprising administering to the subject a therapeutically effective amount of a cytokine-MAb DNL construct. In preferred embodiments, the cytokine-MAb DNL construct is a 20-2b construct, as described in further detail in the Examples below.

The administration of cytokine-MAb DNL construct can be supplemented by administering concurrently or sequentially a therapeutically effective amount of another antibody that binds to or is reactive with another antigen on the surface of the target cell. Preferred additional MAbs comprise at least one humanized, chimeric or human MAb selected from the group consisting of a MAb reactive with CD4, CD5, CD8, CD14, CD15, CD16, CD19, IGF-1R, CD20, CD21, CD22, CD23, CD25, CD30, CD32b, CD33, CD37, CD38, CD40, CD40L, CD45, CD46, CD52, CD54, CD70, CD74, CD79a, CD80, CD95, CD126, CD133, CD138, CD154, CEACAM5, CEACAM6, B7, AFP, PSMA, EGP-1, EGP-2, carbonic anhydrase IX, PAM4 antigen, MUC1, MUC2, MUC3, MUC4, MUC5, Ia, MIF, HM1.24, HLA-DR, tenascin, Flt-3, VEGFR, PlGF, ILGF, IL-6, IL-25, tenascin, TRAIL-R1, TRAIL-R2, complement factor C5, oncogene product, or a combination thereof. Various antibodies of use, such as anti-CD19, anti-CD20, and anti-CD22 antibodies, are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996), U.S. Pat. Nos. 5,798,554; 6,187,287; 6,306,393; 6,676,924; 7,109,304; 7,151,164; 7,230,084; 7,230,085; 7,238,785; 7,238,786; 7,282,567; 7,300,655; 7,312,318; and U.S. Patent Application Publ. Nos. 20080131363; 20080089838; 20070172920; 20060193865; 20060210475; 20080138333; and 20080146784, each incorporated herein by reference.

The cytokine-MAb DNL construct therapy can be further supplemented with the administration, either concurrently or sequentially, of at least one therapeutic agent. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

The cytokine-MAb DNL construct can be formulated according to known methods to prepare pharmaceutically useful compositions, whereby the cytokine-MAb DNL construct is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The cytokine-MAb DNL construct can be formulated for intravenous administration via, for example, bolus injection or continuous infusion. Preferably, cytokine-MAb DNL construct is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the cytokine-MAb DNL construct. Control release preparations can be prepared through the use of polymers to complex or adsorb the cytokine-MAb DNL construct. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release from such a matrix depends upon the molecular weight of the cytokine-MAb DNL construct, the amount of cytokine-MAb DNL construct within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The cytokine-MAb DNL construct may also be administered to a mammal subcutaneously or even by other parenteral routes. Moreover, the administration may be by continuous infusion or by single or multiple boluses. Preferably, the cytokine-MAb DNL construct is infused over a period of less than about 4 hours, and more preferably, over a period of less than about 3 hours.

More generally, the dosage of an administered cytokine-MAb DNL construct for humans will vary depending upon such factors as the patient's age, weight, height, sex, general medical condition and previous medical history. It may be desirable to provide the recipient with a dosage of cytokine-MAb DNL construct that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, a cytokine-MAb DNL construct may be administered as one dosage every 2 or 3 weeks, repeated for a total of at least 3 dosages. Or, the construct may be administered twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In preferred embodiments, the cytokine-MAb DNL constructs are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). Cancers conducive to treatment methods of the present invention involves cells which express, overexpress, or abnormally express IGF-1R.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Kits

Various embodiments may concern kits containing components suitable for treating or diagnosing diseased tissue in a patient. Exemplary kits may contain at least one or more cytokine-MAb constructs as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, a therapeutic agent may be provided in the form of a prefilled syringe or autoinjection pen containing a sterile, liquid formulation or lyophilized preparation.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

Expression Vectors

Still other embodiments may concern DNA sequences comprising a nucleic acid encoding a cytokine-MAb construct, or its constituent fusion proteins. Fusion proteins may comprise an antibody or cytokine attached to a different peptide or protein, such as the AD and DDD peptides utilized for DNL construct formation as discussed in more detail in the Examples below.

Various embodiments relate to expression vectors comprising the coding DNA sequences. The vectors may contain sequences encoding the light and heavy chain constant regions and the hinge region of a human immunoglobulin to which may be attached chimeric, humanized or human variable region sequences. The vectors may additionally contain promoters that express the encoded protein(s) in a selected host cell, enhancers and signal or leader sequences. Vectors that are particularly useful are pdHL2 or GS. More preferably, the light and heavy chain constant regions and hinge region may be from a human EU myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine. See Edelman et al., *Proc. Natl. Acad. Sci USA* 63: 78-85 (1969). In other embodiments, an IgG1 sequence may be converted to an IgG4 sequence.

The skilled artisan will realize that methods of genetically engineering expression constructs and insertion into host cells to express engineered proteins are well known in the art and a matter of routine experimentation. Host cells and methods of expression of cloned antibodies or fragments have been described, for example, in U.S. patent application Ser. No. 11/187,863, filed Jul. 25, 2005; Ser. No. 11/253,666, filed Oct. 20, 2005 and Ser. No. 11/487,215, filed Jul. 14, 2006, each incorporated herein by reference in its entirety.

EXAMPLES

The following examples are provided to illustrate, but not to limit, the claims of the present invention.

General Methods

Cell Lines.

Cell lines suitable for transfection and protein production are known in the art, such as Sp/EEE and Sp/ESF cells (see, e.g., U.S. Pat. Nos. 7,531,327; 7,537,930 and 7,608,425, the Examples section of each of which is incorporated herein by reference.) Sp/ESF cells, an enhanced variant of Sp2/0-Ag14 (ATCC, Manassas, Va.), were maintained in Hybridoma Serum-Free Media (H-SFM) supplemented with 2 mM L-glutamine and 100 units/mL penicillin-streptomycin. Daudi, Ramos, Raji, NAMALWA and Jeko-1 (ATCC) human lymphomas were maintained in RPMI 1640 media containing 10% FBS and supplemented with 1 mM sodium pyruvate, 10 mM L-glutamine, 25 mM HEPES, and 100 units/mL penicillin-streptomycin.

MAb-IFNα Constructs.

20-2b was produced by DNL via the combination of two DNL modules, $C_{H3}$-AD2-IgG-v-mab and IFNα2b-DDD2, which were each expressed in Sp/ESF. Additional DNL-generated MAb-IFNα constructs, of similar design as 20-2b (humanized IgG1+4 IFNα2b) but with different targeting MAbs, were used as controls in several experiments: 22-2b has $C_{H3}$-AD2-IgG-e-mab (epratuzumab) as its AD2 module, which is directed against CD22 and binds lymphoma; 734-2b has $C_{H3}$-AD2-IgG-h734 as its AD2 module, which is directed against the hapten, In-DTPA and does not bind to any animal proteins or tissues; and R1-2b uses $C_{H3}$-AD2-IgG-hR1, which binds human insulin-like growth factor 1 receptor (IGF-1R).

Analytical Methods.

Protein concentrations of IFNα constructs were measured using a commercial human IFNα2 ELISA kit following the manufacturer's suggested protocol (PBL Interferon Source, Piscataway, N.J.) and confirmed by size-exclusion HPLC performed on a Beckman System Gold Model 116 with a Bio-Sil SEC 250 column (Bio-Rad, Hercules, Calif.) and 0.04 M PBS, pH 6.8, 1 mM EDTA as the mobile phase. Reducing and non-reducing SDS-PAGE analyses were performed using 4-20% gradient Tris-glycine gels (Cambrex Bio Science, Rockland, Me.). All colorimetric (ELISA and MTS), luminescence (reporter) and fluorometric (CDC and ADCC) assays were quantified with an EnVision 2100 multilabel plate reader (PerkinElmer, Waltham, Mass.).

IFNα Activity Measurements.

IFNα2b specific activities were determined using the iLite Human Interferon Alpha Cell-Based Assay Kit following the manufacturer's suggested protocol (PBL Interferon Source). PEGASYS®, 20-2b, and seven more MAb-IFNα constructs were diluted to 10, 2.5 and 0.625 ng/mL in 1% BSA-PBS. PEG-INTRON® was diluted to 1, 0.25 and 0.0625 ng/mL. Each dilution was assayed in triplicate with overnight incubation with the supplied cells. Specific activities were extrapolated from a standard curve generated with the supplied standard. Antiviral activities were determined with an in vitro viral challenge assay using encephalomyocarditis (EMC) virus on A549 cells by an independent analytical laboratory (PBL Interferon Source).

In Vitro Proliferation.

Daudi or Jeko-1 were plated at 5,000 cells/well in 96-well plates and incubated at 37° C. for four (Daudi) or five (Jeko-1) days in the presence of increasing concentrations of the indicated agents. Viable cell densities were determined using a CellTiter 96 Cell Proliferation Assay (Promega, Madison, Wis.).

Ex-Vivo Depletion of Daudi and Ramos Lymphoma Cells from Whole Blood.

The effects of 20-2b on NHL cells as well as peripheral blood lymphocytes in whole human blood from health volunteers were evaluated ex-vivo using flow cytometry and compared to those of v-mab, 734-2b or a combination of v-mab and 734-2b. Daudi or Ramos ($5 \times 10^4$ cells) were mixed with heparinized whole blood (150 µl) and incubated with test MAbs at 0.01, 0.1 or 1 nM for 2 days at 37° C. and 5% $CO_2$. Cells were stained with FITC-labeled anti-CD3, anti-CD19, or mouse $IgG_1$ isotype control (BD Biosciences, San Jose, Calif.). Following lysis of erythrocytes, cells were analyzed using a FACSCalibur (BD Biosciences) with Cell Quest software. Both Daudi and Ramos cells are CD19+ and in the monocyte gate. The normal B- and T-cells are CD19+ and CD3+ cells, respectively, in the lymphocyte gate. Student t-test was used to evaluate statistical significance (P<0.05). In vivo efficacy in mice. Studies were performed in female C.B.17 homozygous severe combined immune deficient (SCID) mice of approximately 20 g (Taconic, Germantown, N.Y.). Each mouse was inoculated i.v. with $1.5 \times 10^7$ Daudi, $2.5 \times 10^6$ Raji or $5 \times 10^6$ NAMALWA cells on day 0. Treatment doses were all administered by subcutaneous injection. Saline was used as a control treatment. Animals monitored daily were humanely sacrificed when hind-limb paralysis developed or if they became otherwise moribund. Additionally, mice were sacrificed if they lost more than 20% of initial body weight. Survival curves were analyzed using Kaplan-Meier plots (log-rank analysis), using the Prism (v4.03) software package (GraphPad Software, Inc.). Some outliers determined by critical Z test were censored from analyses.

Example 1. $C_{H3}$-AD2-IgG Expression Vectors

The pdHL2 mammalian expression vector has been used for the expression of recombinant IgGs (Qu et al., Methods 2005, 36:84-95). A plasmid shuttle vector was produced to facilitate the conversion of any IgG-pdHL2 vector into a $C_{H3}$-AD2-IgG-pdHL2 vector. The gene for the Fc ($C_{H2}$ and $C_{H3}$ domains) was amplified by PCR using the pdHL2 vector as a template and the following oligonucleotide primers:

Fc BglII Left
(SEQ ID NO: 21)
AGATCTGGCGCACCTGAACTCCTG

Fc Bam-EcoRI Right
(SEQ ID NO: 22)
GAATTCGGATCCTTTACCCGGAGACAGGGAGAG.

The amplimer was cloned in the pGemT PCR cloning vector (Promega). The Fc insert fragment was excised from pGemT with Xba I and Bam HI and ligated with AD2-pdHL2 vector that was prepared by digesting h679-Fab-AD2-pdHL2 (Rossi et al., Proc Natl Acad Sci USA 2006, 103:6841-6) with Xba I and Bam HI, to generate the shuttle vector Fc-AD2-pdHL2. To convert IgG-pdHL2 expression vectors to a $C_{H3}$-AD2-IgG-pdHL2 expression vectors, an 861 bp BsrG I/Nde I restriction fragment was excised from the former and replaced with a 952 bp BsrG I/Nde I restriction fragment excised from the Fc-AD2-pdHL2 vector. The following is a partial list of $C_{H3}$-AD2-IgG-pdHL2 expression vectors that have been generated and used for the production of recombinant humanized IgG-AD2 modules:

$C_{H3}$-AD2-IgG-hA20 (anti-CD20)
$C_{H3}$-AD2-IgG-hLL2 (anti-CD22)
$C_{H3}$-AD2-IgG-hL243 (anti-HLA-DR)
$C_{H3}$-AD2-IgG-hLL1 (anti-CD74)
$C_{H3}$-AD2-IgG-hR1 (anti-IGF-1R)
$C_{H3}$-AD2-IgG-h734 (anti-Indium-DTPA).

Example 2. Production of $C_{H3}$-AD2-IgG

Transfection and Selection of Stable $C_{H3}$-AD2-IgG Secreting Cell Lines

All cell lines were grown in Hybridoma SFM (Invitrogen, Carlsbad Calif.). $C_{H3}$-AD2-IgG-pdHL2 vectors (30 µg) were linearized by digestion with Sal I restriction endonuclease and transfected into Sp2/0-Ag14 ($2.8 \times 10^6$ cells) by electroporation (450 volts, 25 µF). The pdHL2 vector contains the gene for dihydrofolate reductase allowing clonal selection as well as gene amplification with methotrexate (MTX).

Following transfection, the cells were plated in 96-well plates and transgenic clones were selected in media containing 0.2 µM MTX. Clones were screened for $C_{H3}$-AD2-IgG productivity by a sandwich ELISA using 96-well microtitre plates coated with specific anti-idiotype MAbs. Conditioned media from the putative clones were transferred to the micro-plate wells and detection of the fusion protein was accomplished with horseradish peroxidase-conjugated goat anti-human IgG F(ab')$_2$ (Jackson ImmunoResearch Laboratories, West Grove, Pa.). Wells giving the highest signal were expanded and ultimately used for production.

Production and Purification of $C_{H3}$-AD2-IgG Modules

For production of the fusion proteins, roller bottle cultures were seeded at $2 \times 10^5$ cells/ml and incubated in a roller bottle incubator at 37° C. under 5% $CO_2$ until the cell viability dropped below 25% (~10 days). Culture broth was clarified by centrifugation, filtered, and concentrated up to 50-fold by ultrafiltration. For purification of $C_{H3}$-AD2-IgG modules, concentrated supernatant fluid was loaded onto a Protein-A (MAB Select) affinity column. The column was washed to baseline with PBS and the fusion proteins were eluted with 0.1 M Glycine, pH 2.5.

Example 3. Generation of DDD-Module Based on Interferon (IFN)-α1b

Construction of IFN-α2b-DDD2-pdHL2 for Expression in Mammalian Cells

The cDNA sequence for IFN-α2b was amplified by PCR resulting in sequences comprising the following features, in which XbaI and BamHI are restriction sites, the signal peptide is native to IFN-α2b, and 6 His is a hexahistidine tag: XbaI-Signal peptide-IFNα2b-6 His-BamHI (6 His disclosed as SEQ ID NO: 28). The resulting secreted protein consisted of IFN-α2b fused at its C-terminus to a polypeptide of the following sequence:

(SEQ ID NO: 23)
KSHHHHHHGSGGGGSGGGCGHIQIPPGLTELLQGYTVEVLRQQPPDLVE
FAVEYFTRLREARA.

PCR amplification was accomplished using a full length human IFNα2b cDNA clone (Invitrogen Ultimate ORF human clone cat# HORF01Clone ID IOH35221) as a template and the following oligonucleotides as primers:

IFNA2 XbaI Left
(SEQ ID NO: 24)
TCTAGACACAGGACCTCATCATGGCCTTGACCTTTGCTTTACTGG

IFNA2 BamHI right
(SEQ ID NO: 25)
GGATCCATGATGGTGATGATGGTGTGACTTTTCCTTACTTCTTAAACTTT
CTTGC The PCR amplimer was cloned into the pGemT vector. A DDD2-pdHL2 mammalian expression vector was prepared for ligation with IFN-α2b as follows. The $C_{H1}$-DDD2-Fab-hMN-14-pdHL2 (Rossi et al., Proc Natl Acad Sci USA 2006, 103:6841-6) vector was digested with Xba I and Bam HI, which removes all of the Fab gene sequences but leaves the DDD2 coding sequence. The IFN-α2b amplimer was excised from pGemT with Xba I and Bam HI and ligated into the DDD2-pdHL2 vector to generate the expression vector IFN-α2b-DDD2-pdHL2.

Mammalian Cell Expression of IFN-α2b-DDD2

IFN-α2b-DDD2-pdHL2 was linearized by digestion with Sal I and stably transfected by electroporation into Sp/ESF myeloma cells (see U.S. patent application Ser. No. 11/877,728, the Examples section of which is incorporated herein by reference). Two clones were found to have detectable levels of IFN-α2b by ELISA. One of the two clones, designated 95, was adapted to growth in serum-free media without substantial decrease in productivity. The clone was subsequently amplified with increasing MTX concentrations from 0.1 to 0.8 μM over five weeks. At this stage, it was sub-cloned by limiting dilution and the highest producing sub-clone (95-5) was expanded. The productivity of 95-5 grown in shake-flasks was estimated to be 2.5 mg/L using commercial rIFN-α2b (Chemicon IF007, Lot 06008039084) as standards.

Purification of IFN-α2b-DDD2 from Batch Cultures Grown in Roller Bottles

Clone 95-5 was expanded to 34 roller bottles containing a total of 20 L of serum-free Hybridoma SFM with 0.8 μM MTX and allowed to reach terminal culture. The culture broth was processed and IFN-α2b-DDD2 was purified by immobilized metal affinity chromatography (IMAC) as follows. The supernatant fluid was clarified by centrifugation, 0.2 μM filtered, diafiltered into 1× Binding buffer (10 mM imidazole, 0.5 M NaCl, 50 mM NaH$_2$PO$_4$, pH 7.5), concentrated to 310 mL, added Tween 20 to a final concentration of 0.1%, and loaded onto a 30-mL Ni-NTA column. Following sample loading, the column was washed with 500 mL of 0.02% Tween 20 in 1× binding buffer and then 290 mL of 30 mM imidazole, 0.02% Tween 20, 0.5 M NaCl, 50 mM NaH$_2$PO$_4$, pH 7.5. The product was eluted with 110 mL of 250 mM imidazole, 0.02% Tween 20, 150 mM NaCl, 50 mM NaH$_2$PO$_4$, pH 7.5. Approximately 6 mg of IFNα2b-DDD2 was purified.

Production of IFN-α2b-DDD2 in *E. coli*

IFN-α2b-DDD2 was also expressed by microbial fermentation as a soluble protein in *E. coli*. The coding sequence was amplified by PCR using IFN-α2b-DDD2-pdHL2 DNA as a template. The amplimer was cloned into the pET26b *E. coli* expression vector using Nde I and Xho I restriction sites. Protein was expressed intracellularly in BL21pLysS host cells by induction of LB shake flasks with 100 μM IPTG at 18° C. for 12 hours. Soluble IFN-α2b-DDD2 was purified from cell lysates by IMAC as described above.

Example 4. Generation of a DNL Conjugate Comprising Four IFN-α2b-DDD2 Moieties Linked to $C_{H3}$-AD2-IgG A DNL complex comprising four IFN-α2b-DDD2 moieties linked to $C_{H3}$-AD2-IgG (FIG. 1) was made as follows. Briefly, a select $C_{H3}$-AD2-IgG was combined with approximately two mole-equivalents of IFN-α2b-DDD2 and the mixture was reduced under mild conditions overnight at room temperature after adding 1 mM EDTA and 2 mM reduced glutathione (GSH). Oxidized glutathione was added to 2 mM and the mixture was held at room temperature for an additional 12-24 hours. The DNL conjugate was purified over a Protein A affinity column. Four such DNL conjugates designed 20-2b, 22-2b, hR1-2b, and 243-2b, each comprising four copies of IFN-α2b anchored on $C_{H3}$-AD2-IgG-hA20 (with specificity for CD20), $C_{H3}$-AD2-IgG-hLL2 (with specificity for CD22), $C_{H3}$-AD2-IgG-hR1 (with specificity for IGF-1R) and $C_{H3}$-AD2-IgG-hL243 (with specificity for HLA-DR), respectively, were prepared. SE-HPLC analyses of 20-2b generated from mammalian (m) or *E. coli* (e)-produced IFN-α2b-DDD2 each showed a major peak having a retention time consistent with a covalent complex composed of an IgG and 4 IFN-α2b groups (not shown). Similar SE-HPLC profiles were observed for the other three IFN-IgG conjugates.

Example 5. In Vitro Activity of the IFN-IgG Conjugates

The in vitro IFNα biological activity of 20-2b was compared to that of commercial PEGylated IFNα2 agents, PEGASYS® and PEG-INTRON®, using cell-based reporter, viral protection, and lymphoma proliferation assays. Specific activities were determined using a cell-based kit, which utilizes a transgenic human pro-monocyte cell line carrying a reporter gene fused to an interferon-stimulated response element (FIG. 2A-2D). The specific activity of 20-2b (5300 IU/pmol) was greater than both PEGASYS® (170 IU/pmol) and PEG-INTRON® (3400 IU/pmol) (FIG. 2A). 734-2b, 1R-2b and five additional MAb-IFNα constructs (data not shown), which were produced similarly to 20-2b, each exhibited similar specific activities (4000-8000 IU/pmol), demonstrating the consistency of the DNL method for generating such structures (FIG. 2A). Having four IFNα2b groups contributed to the enhanced potency of MAb-IFNα. When normalized to IFNα equivalents, the specific activity/IFNα was about 10-fold greater than PEGASYS® and only about 2-fold less than PEG-INTRON®.

Comparison of MAb-IFNα, PEGASYS® and PEG-INTRON® in an in vitro viral protection assay demonstrated that MAb-IFNα retains IFNα2b antiviral activity with specific activities similar to PEG-INTRON® and 10-fold greater than PEGASYS® (FIG. 2B).

IFNα2b can have a direct antiproliferative or cytotoxic effect on some tumor lines. The activity of 20-2b was measured in an in vitro proliferation assay with a Burkitt lymphoma cell line (Daudi) that is highly sensitive to IFNα (FIG. 2C). Each of the IFNα2 agents efficiently inhibited (>90%) Daudi in vitro with high potency ($EC_{50}$=4-10 pM). However, 20-2b ($EC_{50}$=0.25 pM) was about 30-fold more potent than the non-targeting MAb-IFNα constructs. The parent anti-CD20 MAb of 20-2b has anti-proliferative activity in vitro on many lymphoma cell lines, including Daudi (Rossi et al., 2008, Cancer Res 68:8384-92), at considerably greater concentrations ($EC_{50}$>10 nM). The in vitro activity of 20-2b was also assessed using Jeko-1, which is a mantle cell lymphoma line that has lower sensitivity to both IFNα and anti-CD20 (FIG. 2D). Jeko-1 is only modestly sensitive to the parent anti-CD20 MAb, having 10% maximal inhibition ($I_{max}$) with an $EC_{50}$ near 1 nM. As shown with 734-2b, Jeko-1 ($I_{max}$=43%; $EC_{50}$=23 pM) is less responsive to IFNα2b than Daudi ($I_{max}$=90%; $EC_{50}$=7.5 pM). Compared to 734-2b, 20-2b inhibited Jeko-1 to a greater extent ($I_{max}$=65%) and exhibited a biphasic dose-response curve (FIG. 2D). At <10 pM, a low-concentration response attributed to IFNα2b activity was observed, which plateaus at $I_{max}$=43%, similar to 734-2b. A high-concentration response was evident above 100 pM, where $I_{max}$ reached 65%. The low-concentration IFNα2b response of 20-2b ($EC_{50}$=0.97 pM) was 25-fold more potent than 734-2b, similar to the results with Daudi.

A combination of the parent anti-CD20 antibody and 734-2b (v-mab+734-2b) was assayed to elucidate whether the increased potency of 20-2b is due to an additive/synergistic effect of CD20 and IFNα signaling. The dose response curve for v-mab+734-2b was largely similar to 734-2b alone, except at >1 nM, where inhibition increased for the former but not the latter. These results suggest that MAb targeting is responsible for the lower $EC_{50}$ of 20-2b, but its greater $I_{max}$ is apparently due to the additive activity of IFNα2b and CD-20 signaling. The effect of CD20 signaling was only evident in the high-concentration response for 20-2b ($EC_{50}$=0.85 nM), which parallels the response to v-mab ($EC_{50}$=1.5 nM). A biphasic dose-response curve was not obvious for v-mab+734-2b, because the two responses overlap. However, an additive effect was evident at >1 nM concentrations. The $I_{max}$ of 20-2b (65%) was greater than the added responses of IFNα2b ($I_{max}$=43%) and v-mab ($I_{max}$=10%), suggesting possible synergism between the actions of IFNα2b and v-mab.

ADCC Activity

Figure 4B:
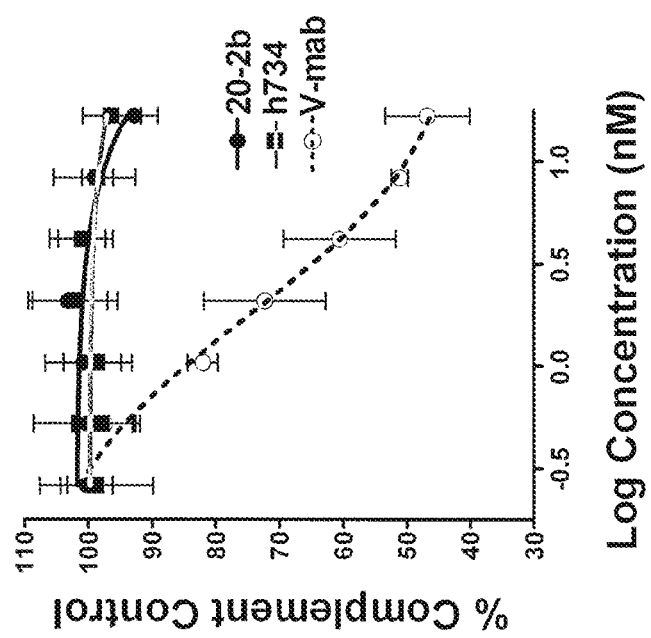
FIG. 4B shows CDC effector functions of 20-2B. Daudi cells were incubated with serial dilutions of 20-2b (●), 734-2b (■) or v-mab (○) in the presence of human complement. The % complement control (number of viable cells in the test sample compared to cells treated with complement only) was plotted vs. the log of the nM concentration. Error bars, SD.
Figure 4A:
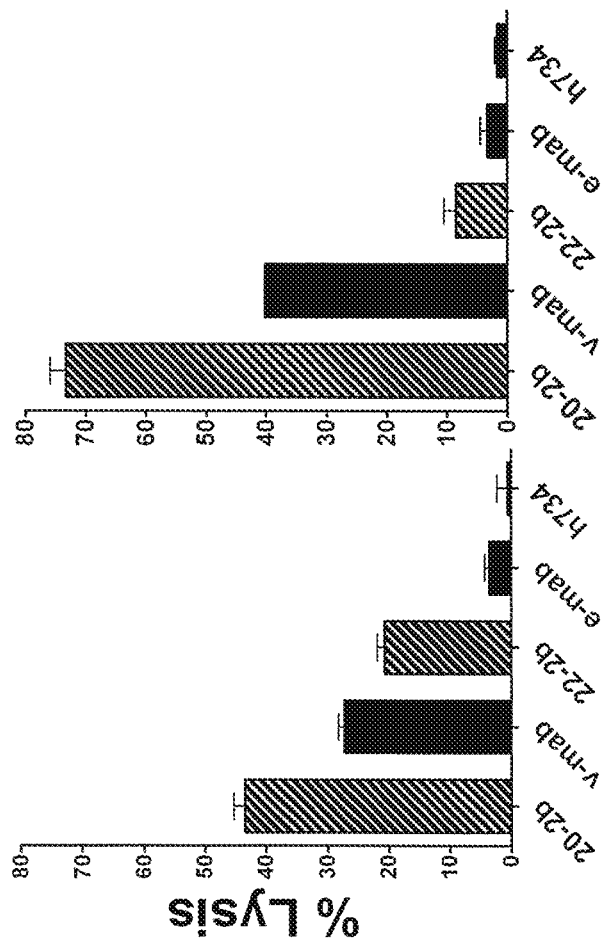
FIG. 4A illustrates ADCC effector functions of 20-2b. Daudi or Raji cells were incubated with 20-2b, 22-2b, v-mab, epratuzumab (e-mab), or h734 at 5 µg/ml in the presence of freshly isolated PBMCs for 4 h before quantification of cell lysis.

IFNα can potentiate ADCC activity, which is a fundamental mechanism of action (MOA) for anti-CD20 immunotherapy, by activating NK cells and macrophages. We compared ADCC of 20-2b and v-mab with two NHL cell lines using peripheral blood mononuclear cells (PBMCs) as effector cells. Replicate assays using PBMCs from multiple donors consistently demonstrated that 20-2b had enhanced ADCC compared to v-mab, as shown for both Daudi and Raji cells (FIG. 4A). This effect was also shown with 22-2b, a MAb-IFNα comprising the anti-CD22 MAb, epratuzumab, which shows modest ADCC (Carnahan et al., 2007, Mol Immunol 44:1331-41.

CDC Activity

CDC is thought to be an important MOA for Type-I anti-CD20 MAbs (including v-mab and rituximab). However, this function is lacking in the Type-II MAbs, represented by tositumomab (Cardarelli et al., 2002, Cancer Immunol Immunother 51:15-24), which nonetheless has anti-lymphoma activity. Unlike v-mab, 20-2b does not show CDC activity in vitro (FIG. 4B). These results are consistent with those for other DNL structures based on the $C_{H3}$-AD2-IgG-v-mab module, in which complement fixation is apparently impaired, perhaps by steric interference (Rossi et al., 2008).

Example 6. Pharmacokinetic (PK) Analysis of 20-2b

The pharmacokinetic (PK) properties of 20-2b were evaluated in male Swiss-Webster mice and compared to those of PEGASYS®, PEG-INTRON and α2b-413 (Pegylated IFN made by DNL, see U.S. patent application Ser. No. 11/925,408). Concentrations of IFN-α in the serum samples at various times were determined by ELISA following the manufacturer's instructions. Briefly, the serum samples were diluted appropriately according to the human IFN-α standard provided in the kit. An antibody bound to the microtiter plate wells captures interferon. A second antibody was then used to reveal the bound interferon, which was quantified by anti-secondary antibody conjugated to horseradish peroxidase (HRP) following the addition of Tetramethyl benzidine (TMB). The plates were read at 450 nm. FIG. 3 presents the results of the PK analysis, which showed significantly slower elimination and longer serum residence of 20-2b compared to the other agents. At an injected dose of 210 pmol, the calculated pharmacokinetic serum half-life in hours was 8.0 hr (20-2b), 5.7 hr (α2b-413), 4.7 hr (PEGASYS®) and 2.6 hr (PEG-INTRON). The elimination rate (1/h) was 0.087 (20-2b), 0.121 (α2b-413), 0.149 (PEGASYS®) and 0.265 (PEG-INTRON). The calculated $MRT_{0.08} \to \infty$ (hr) was 22.2 (20-2b), 12.5 (α2b-413), 10.7 (PEGASYS®) and 6.0 (PEG-INTRON). Because the pharmacokinetic parameters are determined more by the nature of the complex than the individual antibody or cytokine, it is expected that the PK characteristics of the cytokine-DNL complex are generalizable to other cytokine moieties and antibody moieties and are not limited to the specific 20-2b construct discussed above.

Example 7. In Vivo Activity of 20-2b

Serum Stability.

20-2b was stable in human sera (≥10 days) or whole blood (≥6 days) at 37° C. (not shown). Concentration of 20-2b complex was determined using a bispecific ELISA assay. There was essentially no detectable change in serum 20-2b levels in either whole blood or serum over the time period of the assay.

Ex Vivo Efficacy of 20-2b Against Lymphoma Cells from Whole Human Blood

Figure 5:
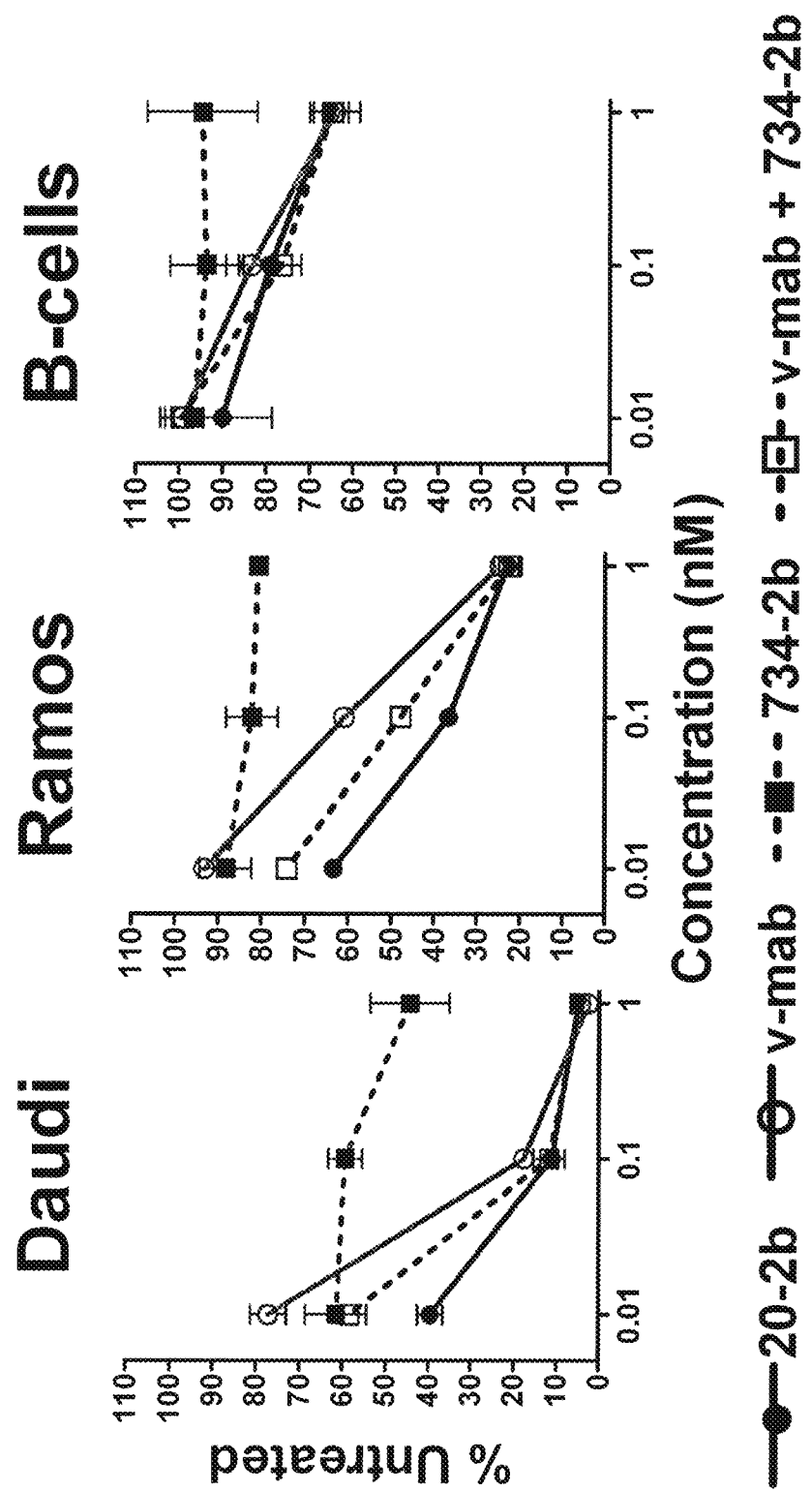
FIG. 5 shows enhanced depletion of NHL cells from whole blood by 20-2b. Fresh heparinized human blood was mixed with either Daudi or Ramos and incubated with 20-2b (●), v-mab (○), 734-2b (■) or v-mab+734-2b (□) at 0.01, 0.1 or 1 nM for two days. The effect of the indicated treatments on lymphoma and peripheral blood lymphocytes was evaluated using flow cytometry. Error bars, SD.

We compared the abilities of 20-2b, v-mab, 734-2b, or v-mab+734-2b to eliminate lymphoma or normal B-cells from whole blood in an ex vivo setting (FIG. 5). The therapeutic efficacy of naked anti-CD20 MAbs is believed to be achieved via three mechanisms of action (MOA)-signaling-induced apoptosis or growth arrest, ADCC, and CDC (Glennie et al., 2007, Mol Immunol 44:3823-37). In this assay, v-mab can employ all three MOA, while, based on the in vitro findings, 20-2b can potentially take advantage of signaling and enhanced ADCC, but not CDC. In this short-term model, the IFNα2b groups of 20-2b and 734-2b can act directly on tumor cells, augment the ADCC activity of v-mab, and possibly have some immunostimulatory effects. However, the full spectrum of IFNα-mediated activation of the innate and adaptive immune systems that might occur in vivo is not realized in this two-day ex vivo assay.

At 0.01 nM, 20-2b depleted Daudi cells (60.5%) significantly more than v-mab (22.8%), 734-2b (38.6%) or v-mab+734-2b (41.7%) (FIG. 5). At 0.1 nM, 20-2b and v-mab+734-2b depleted Daudi to a similar extent (88.9%), which was more than for v-mab (82.4%) or 734-2b (40.7%) (FIG. 5). At 1 nM, each agent depleted Daudi >95%, except for 734-2b (55.7%) (FIG. 5). Each of the differences indicated were statistically significant (P<0.01).

Ramos is less sensitive than Daudi to both IFNα2b and v-mab. The effect of 734-2b was only moderate, resulting in <20% depletion of Ramos at each concentration (FIG. 5). At both 0.01 and 0.1 nM, 20-2b depleted Ramos more than v-mab+734-2b, which in turn eliminated more cells than v-mab (FIG. 5). At 1 nM, all treatments besides 734-2b resulted in similar Ramos depletion (75%) (FIG. 5). Each of the differences indicated were statistically significant (P<0.02).

As demonstrated with 734-2b, IFNα2b alone does not deplete normal B-cells in this assay. At these low concentrations, 20-2b, v-mab, and v-mab+734-2b each show similar dose-responsive depletion of B-cells, which is markedly less than the depletion of either Daudi or Ramos. None of the treatments resulted in significant depletion of T-cells (data not shown).

In Vivo Efficacy of 20-2b in SCID Mice

Figure 6A:
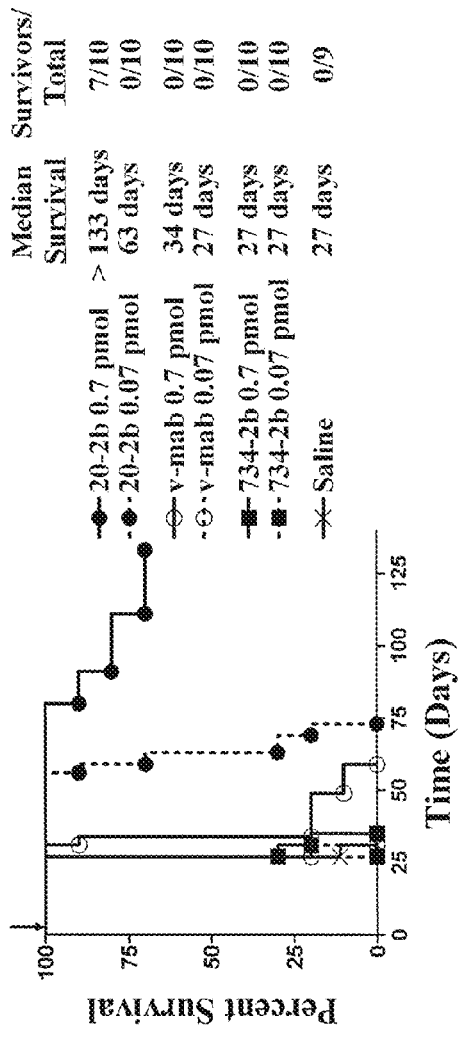
FIG. 6A illustrates survival curves showing therapeutic efficacy of 20-2b in a disseminated Burkitt's lymphoma (Daudi) xenograft model. Female C.B. 17 SCID mice were administered Daudi cells i.v. on day 0. Treatments consisted of 20-2b (●), 734-2b (■), v-mab (○), PEGASYS® (▼) or saline (X) given as a single s.c. doses. Days of treatment are indicated with arrows. Survival curves were analyzed using Prism software. In an Early Daudi model. Groups of 10 mice were given a single dose of 0.7 pmol (solid line) or 0.07 pmol (dashed line) on day 1.

A limitation of the mouse model is the very low sensitivity of murine cells to human IFNα2b. The overall therapeutic advantage of 20-2b that might be achieved in humans can involve the enhancement of both innate and adaptive immunity. With these limitations in mind, we studied the anti-lymphoma in vivo efficacy of 20-2b against disseminated Burkitt lymphoma models in SCID mice. We initially tested a highly sensitive early Daudi model (FIG. 6A). One day after inoculation, groups were administered a single low dose of 20-2b, v-mab, or 734-2b. A single dose of v-mab or 734-2b at 0.7 pmol (170 ng) resulted in significant improvement in survival when compared to saline for v-mab (P<0.0001), but not for the irrelevant MAb-IFNα control, 734-2b (FIG. 6A). This improvement was modest, with the median survival time (MST) increasing from 27 days for saline to 34 days for v-mab. However, a single dose of 0.7 pmol (170 ng) of 20-2b improved the MST by more than 100 days over both saline control and v-mab groups (P<0.0001) (FIG. 6A). The study was terminated after 19 weeks, at which time the 7 long-term survivors (LTS) in the 0.7 pmol 20-2b treatment group were necropsied with no visible evidence of disease found (cured) (FIG. 6A). Remarkably, even the lowest dose of 0.07 pmol (17 ng) of 20-2b more than doubled the MST (FIG. 6A).

Figure 6B:
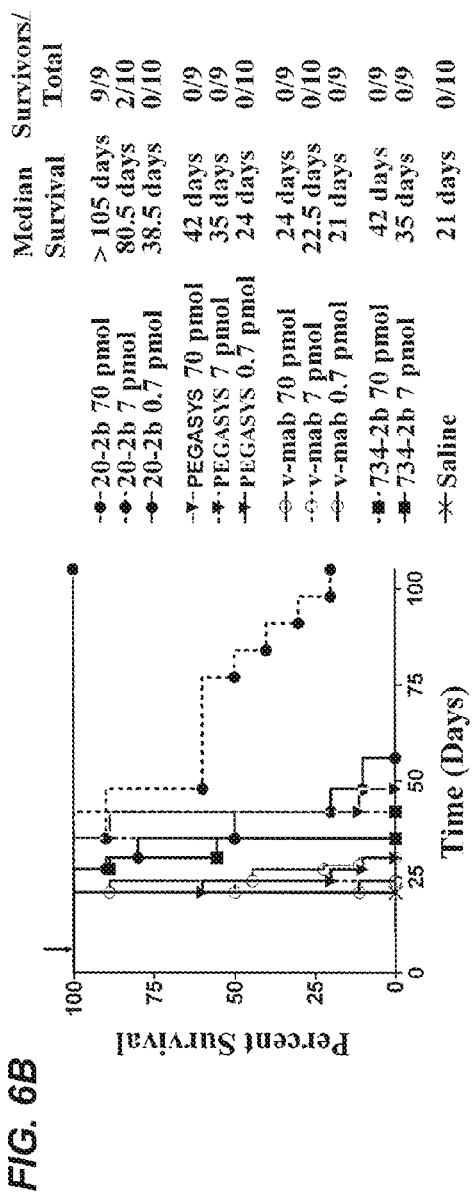
FIG. 6B shows a similar study to FIG. 6(A), but in an Advanced Daudi model. Groups of 10 mice were given a single dose of 0.7 pmol (solid line), 7 pmol (dashed line) or 70 pmol (gray line) on day 7.

Next, we assessed the efficacy of 20-2b in a more challenging advanced Daudi model, in which mice were allowed to develop a substantially greater tumor burden prior to treatment (FIG. 6B). Seven days after tumor inoculation, groups were administered a single low dose (0.7, 7.0 or 70 pmol) of 20-2b, v-mab, 734-2b, or PEGASYS®. The MST for the saline control mice was 21 days (FIG. 6B). The highest dose (70 pmol) of PEGASYS® or 734-2b, each of which have enhanced Pk (compared to recombinant IFNα2b) but do not target tumor, doubled the MST (42 days; P<0.0001) (FIG. 6B). Treatment with 20-2b at a 100-fold lower dose (0.7 pmol) produced similar results (38.5 days) as the highest dose (70 pmol) of either PEGASYS® or 734-2b (FIG. 6B). Treatment with 20-2b at a 10-fold lower dose (7 pmol) resulted in significantly improved survival (80.5 days, 20% LTS) over treatment with 70 pmol of PEGASYS® or 734-2b (P<0.0012) (FIG. 6B). At the highest dose tested (70 pmol), 20-2b improved the MST to >105 days with 100% LTS (FIG. 6B). We have demonstrated previously with the early tumor model that v-mab can increase survival of Daudi-bearing mice at relatively low doses (3.5 pmol) while higher doses result in LTS. However, in this advanced tumor model, a single dose of 70 pmol of v-mab had only a modest, though significant, effect on survival (MST=24 days, P=0.0001) (FIG. 6B).

Figure 7A:
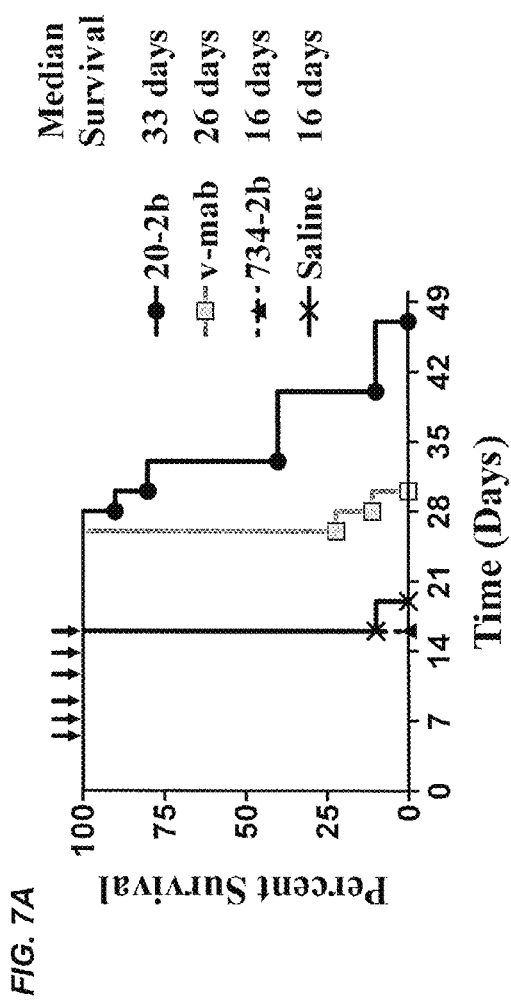
FIG. 7A presents survival curves showing therapeutic efficacy of 20-2b in disseminated Burkitt's lymphoma (Raji and NAMALWA) xenograft models. Female C.B. 17 SCID mice were administered NHL cells i.v. on day 0. Treatments consisted of 20-2b (●), 734-2b (■), v-mab (○) or saline (X) given as s.c. doses. Days of treatment are indicated with arrows. Survival curves were analyzed using Prism software. In an Advanced Raji model, groups of 10 received 250 pmol doses on days 5, 7, 9, 12, 14 and 16.

We subsequently assayed 20-2b in more challenging models, which are less sensitive than Daudi to direct inhibition by IFNα and less responsive to immunotherapy with v-mab. Raji is ~1000-fold less sensitive to the direct action of IFNα2b compared to Daudi. However, Raji has a similar CD20 antigen density to Daudi (Stein et al., 2006, Blood 108:2736-44) and is responsive to v-mab, albeit considerably less so than Daudi (Goldenberg et al., 2009, Blood 113, 1062-70). The efficacy of 20-2b was studied in an advanced Raji model with therapy beginning five days after tumor inoculation (FIG. 7A). Groups were administered a total of 6 injections (250 pmol each) over two weeks. 734-2b did not improve survival over saline (MST=16 days), consistent with the insensitivity of Raji to IFNα (FIG. 7A). V-mab significantly improved survival over saline (MST=26 days, P<0.0001) (FIG. 7A). 20-2b was superior to all other treatments (MST=33 days, P<0.0001) (FIG. 7A).

Figure 7B:
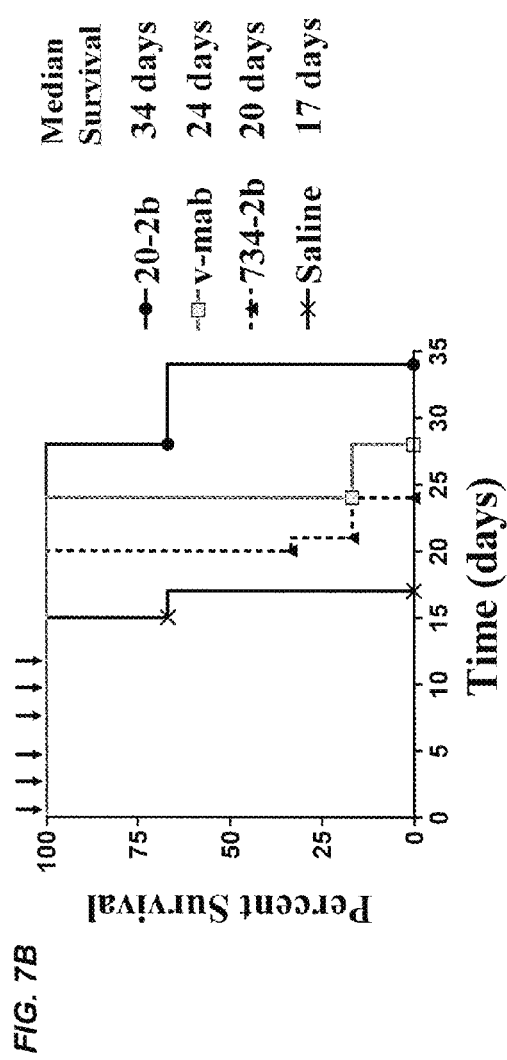
FIG. 7B shows a similar study to FIG. 7(A), but in an Early NAMALWA model. Groups of 6 received 250 pmol doses of 20-2b or 734-2b on days 1, 3, 5, 8, 10 and 12 or 3.5 nmol doses of v-mab on days 1, 5, 9, 13, 17, 21 and 25.

Finally, we investigated the efficacy of 20-2b with NAMALWA (FIG. 7B), a human lymphoma that has low sensitivity to the direct action of IFNα, ~25-fold lower CD20 antigen density compared to Daudi or Raji, and is considered to be resistant to anti-CD20 immunotherapy (Stein et al., 2006). Groups were administered a total of 6 doses (250 pmol each) of either 20-2b or 734-2b. Another group was administered a total of 7 doses (3.5 nmol each) of v-mab. The group treated with saline had an MST of 17 days (FIG. 7B). Treatment with 734-2b very modestly, though significantly, improved survival (MST=20 days, P=0.0012) (FIG. 7B). 20-2b (MST=34 days) was superior to 734-2b (P=0.0004) as well as v-mab (MST=24 days, P=0.0026), which was given at a 14-fold higher dose (FIG. 7B).

Conclusions

The results demonstrate unequivocally that targeting of IFNα with an anti-CD20 MAb makes the immunocytokine more potent and effective than either agent alone or in combination. MAb targeting of IFNα to tumors may allow a less frequent dosing schedule of a single agent, reduce or eliminate side effects associated with IFN therapy, and result in profoundly enhanced efficacy. Additionally, targeted IFNα can induce an acute tumor-directed immune response and possibly evoke immune memory via pleiotropic stimulation of innate and adaptive immunity (Belardelli et al, 2002, Cytokine Growth Factor Rev 12:119-34). Other groups have produced MAb-IFNα made by chemical conjugation that revealed some of the potential clinical benefits of such constructs (Pelham et al., 1983, Cancer Immunol Immunother 15:210-16; Ozzello et al., 1998, Breast Cancer Res Treat 48:135-47). A recombinant MAb-IFNα comprising murine IFNα and an anti-HER2/neu MAb exhibited potent inhibition of a transgenic (HER2/neu) murine B-cell lymphoma in immunocompetent mice and was also capable of inducing a protective adaptive immune response with immunologic memory (Huang et al., 2007, J Immunol 179:6881-88).

We expect that therapy with 20-2b will stimulate localized recruitment and activation of a number of immune cells, including NK, T4, T8, and dendritic cells, resulting in enhanced cytotoxicity and ADCC, and may potentially induce tumor-directed immunologic memory. However, murine cells are exceedingly less sensitive (~4 logs) than human cells to human IFNα2b (Kramer et al., 1983, J Interferon Res 3:425-35; Weck et al., 1981, J Gen Virol 57:233-37). Therefore, very little, if any, of the anti-lymphoma activity of 20-2b in the mouse model in vivo studies described above can be attributed to IFNα2b activation of the mouse immune response. Rather, killing is due primarily to the direct action of IFNα2b on the lymphoma cells.

We have shown that 20-2b has augmented ADCC, which may be the most important MOA of anti-CD20 immunotherapy. However, since human IFNα2b is only a very weak stimulator of the murine host's immune effector cells, an IFNα-enhanced ADCC is probably not realized as it might be in humans. Even with these limitations, the in vivo results demonstrate that 20-2b can be a highly effective anti-lymphoma agent, exhibiting more than 100-times the potency of v-mab or a non-targeting MAb-IFNα in the IFNα-sensitive Daudi model. Even with lymphoma models that are relatively insensitive to the direct action of IFNα (Raji/NAMALWA) or are resistant to anti-CD20 immunotherapy (NAMALWA), 20-2b showed superior efficacy to either v-mab or non-targeted MAb-IFNα.

Fusion of IFNα2b to v-mab increases its in vivo potency by extending circulation times and enabling tumor targeting. The therapeutic significance of Pk was demonstrated in the Daudi model, where the slower clearing PEGASYS® was superior to the faster clearing PEG-INTRON®, which has a higher specific activity (data not shown). 20-2b was considerably more potent than either PEGASYS® or 734-2b, suggesting that lymphoma targeting via the anti-CD20 MAb is critical to its superior potency and efficacy. Surprisingly, the impact of targeting was evident even in the in vitro assays. In the in vitro proliferation experiments, which only allow for lymphoma inhibition via signaling, 20-2b showed activity at a 25-fold lower concentration compared to non-targeting MAb-IFNα, either alone or when combined with v-mab. The ex vivo setting allows the involvement of all three of the anti-CD20 MOA. Even without CDC activity, 20-2b was more effective at depleting lymphoma from blood than IFNα or v-mab, either alone or in combination, demonstrating the significance of targeting. The influence of MAb targeting in the in vitro/ex vivo studies is somewhat surprising, because the MAbs, effector, and target cells are all confined throughout the experiments. We expect that 20-2b will have a substantially greater impact in vivo in human patients.

The IFNα2b and v-mab components of 20-2b can apparently act additively or synergistically, to contribute to its enhanced potency. The in vitro proliferation assays suggest at least an additive effect, which was substantiated with the results of the ex vivo studies where the combination of v-mab and 734-2b was superior to either agent alone. This may be accomplished ex vivo via increased ADCC activity of v-mab as part of 20-2b or when combined with 734-2b, yet ADCC is not functional in the in vitro proliferation assays, suggesting additional mechanisms. The signal transduced by v-mab-bound CD20 may potentiate the IFNα signal, resulting in enhanced potency. Alternatively, the binding of v-mab, which is a slowly internalizing MAb, may prevent the internalization/down-regulation of the Type-I IFN receptors, resulting in a more prolonged and effective IFNα-induced signal.

Example 8. Generation of DDD Module Based on Erythropoeitin (EPO)

Construction of EPO-DDD2-pdHL2 for Expression in Mammalian Cells

The cDNA sequence for EPO was amplified by PCR resulting in sequences comprising the following features, in which Xba I and Bam HI are restriction sites, the signal peptide is native to human EPO, and 6 His is a hexahistidine tag: XbaI-Signal peptide-EPO-6 His-BamHI (6 His disclosed as SEQ ID NO: 28). The resulting secreted protein consists of EPO fused at its C-terminus to a polypeptide consisting of:

```
                                              (SEQ ID NO: 23)
KSHHHHHHGSGGGGSGGGCGHIQIPPGLTELLQGYTVEVLRQQPPDLVE
FAVEYFTRLREARA.
```

PCR amplification was accomplished using a full-length human EPO cDNA clone as a template and the following oligonucleotides as primers:

```
EPO XbaI left
                                              (SEQ ID NO: 26)
TCTAGACACAGGACCTCATCATGGGGGTGCACGAATGTCC EPO BamHI Right
                                              (SEQ ID NO: 27)
GGATCCATGATGGTGATGATGGTGTGACTTTCTGTCCCCTGTCCTGCAG
```

The PCR amplimer was cloned into the pGemT vector. A DDD2-pdHL2 mammalian expression vector was prepared for ligation with EPO by digestion with XbaI and Bam HI restriction endonucleases. The EPO amplimer was excised from pGemT with XbaI and Bam HI and ligated into the DDD2-pdHL2 vector to generate the expression vector EPO-DDD2-pdHL2.

Mammalian Cell Expression of EPO-DDD2

EPO-pdHL2 was linearized by digestion with SalI enzyme and stably transfected into Sp/ESF myeloma cells by electroporation. Clones were selected with media containing 0.15 μM MTX. Clones #41, 49 and 37 each were shown to produce ~0.5 mg/L of EPO by an ELISA using Nunc Immobilizer Nickel-Chelate plates to capture the His-tagged fusion protein and detection with anti-EPO antibody. Approximately 2.5 mg of EPO-DDD2 was purified by IMAC from 9.6 liters of serum-free roller bottle culture.

Example 9. Generation of 734-EPO, a DNL Conjugate Comprising Four EPO-DDD2 Moieties Linked to $C_{H3}$-AD2-IgG-h734

734-EPO was produced as described above for 20-2b. SE-HPLC analysis of the protein A-purified 734-EPO showed a major peak and a shoulder of a higher molecular size (not shown). The retention time of the major peak was consistent with a covalent complex composed of an IgG and 4 EPO groups. The shoulder was likely due to a non-covalent dimer of the IgG-EPO conjugate. SDS-PAGE analysis with Coomassie blue staining and anti-EPO immunoblot analysis showed that under non-reducing conditions the product had a Mr of >260 kDa (not shown), consistent with the deduced MW of ~310 kDa. Under reducing conditions the bands representing the three constituent polypeptides of 734-EPO (EPO-DDD2, Heavy chain-AD2, and light chain) were evident and appeared to be similar in quantity (not shown). Non-product contaminants were not detected.

Figure 8:
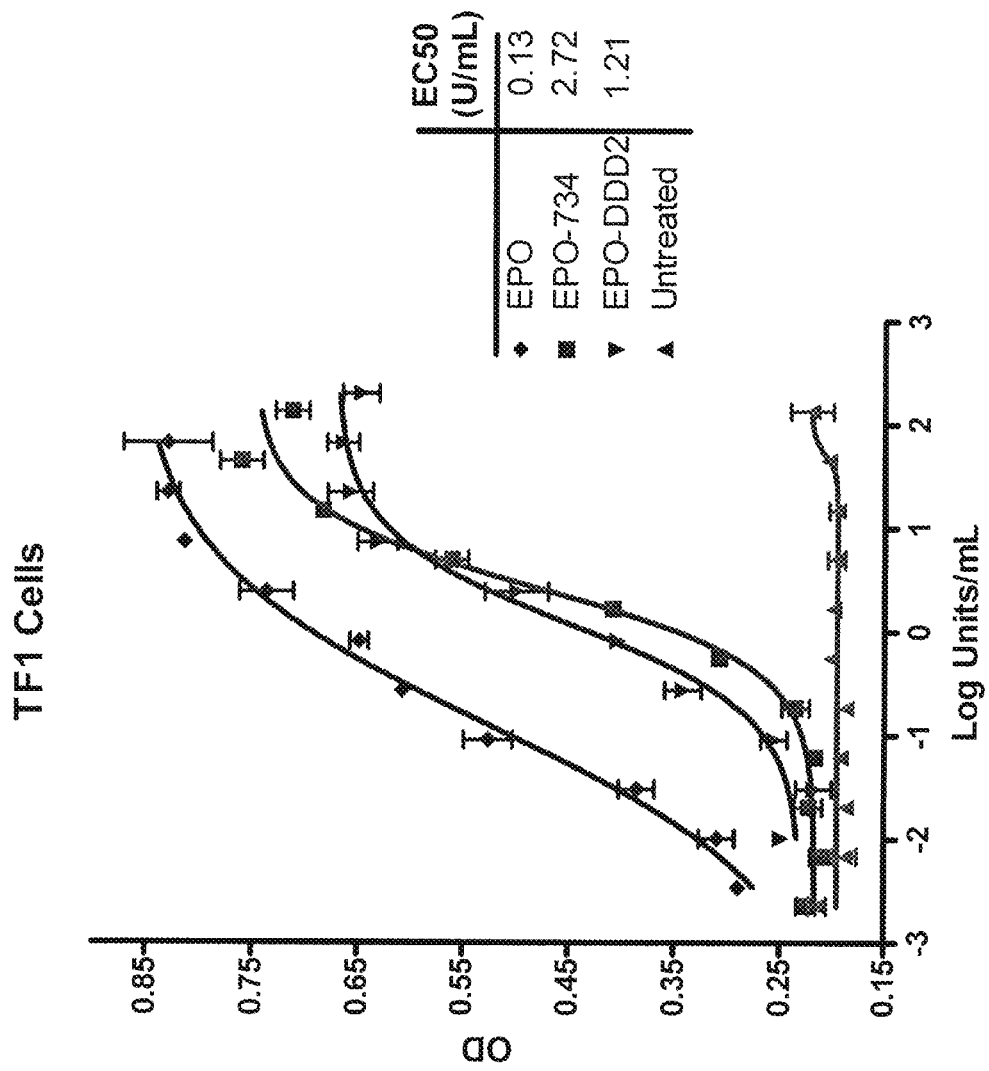
FIG. 8 shows the results of a cell-based assay for EPO activity using TF1 cells that were treated with EPO standard, 734-EPO, or EPO-DDD2 for 72 hours. Dose response curves and $EC_{50}$ values were generated using Graph Pad Prism software.

EPO-DDD2 and 734-EPO were assayed for their ability to stimulate the growth of EPO-responsive TF1 cells (ATCC) using recombinant human EPO (Calbiochem) as a positive control. TF1 cells were grown in RPMI 1640 media supplemented with 20% FBS without GM-CSF supplementation in 96-well plates containing $1 \times 10^4$ cells/well. The concentrations (units/ml) of the EPO constructs were determined using a commercial kit (Human erythropoietin ELISA kit, Stem Cell Research, Cat#01630). Cells were cultured in the presence of rhEPO, EPO-DDD2 or 734-EPO at concentrations ranging from 900 u/ml to 0.001 U/ml for 72 hours. The viable cell densities were compared by MTS assay using 20 µl of MTS reagent/well incubated for 6 hours before measuring the OD490 in a 96-well plate reader. Dose response curves and $EC_{50}$ values were generated using Graph Pad Prism software (FIG. 8). Both EPO-DDD2 and 734-EPO showed in vitro biological activity that was approximately 10% of rhEPO.

Example 10. Generation of DDD Module Based on Granulocyte-Colony Stimulating Factor (G-CSF)

Construction of G-CSF-DDD2-pdHL2 for Expression in Mammalian Cells

The cDNA sequence for G-CSF was amplified by PCR, resulting in sequences comprising the following features in which the signal peptide is native to human G-CSF and 6 His is a hexahistidine tag: Xba I-Signal peptide-G-CSF-6 His-Bam HI (6 His disclosed as SEQ ID NO: 28). The resulting secreted protein consisted of G-CSF fused at its C-terminus to a polypeptide consisting of SEQ ID NO:3.

PCR amplification was accomplished using a full-length human G-CSF cDNA clone (Invitrogen IMAGE human cat#97002RG Clone ID 5759022) as a template and the following oligonucleotides as primers:

G-CSF XbaI Left
(SEQ ID NO: 29)
TCTAGACACAGGACCTCATCATGGCTGGACCTGCCACCCAG

G-CSF BamHI-Right
(SEQ ID NO: 30)
GGATCCATGATGGTGATGATGGTGTGACTTGGGCTGGGCAAGGTGGCGT
AG.

The PCR amplimer was cloned into the pGemT vector. A DDD2-pdHL2 mammalian expression vector was prepared for ligation with G-CSF by digestion with XbaI and Bam HI restriction endonucleases. The G-CSF amplimer was excised from pGemT with XbaI and Bam HI and ligated into the DDD2-pdHL2 vector to generate the expression vector G-CSF-DDD2-pdHL2.

Mammalian Cell Expression of G-CSF-DDD2

G-CSF-pdHL2 was linearized by digestion with Sal I enzyme and stably transfected into Sp/ESF myeloma cells by electroporation. Clones were selected with media containing 0.15 µM MTX. Clone #4 was shown to produce 0.15 mg/L of G-CSF-DDD2 by sandwich ELISA.

Purification of G-CSF-DDD2 from Batch Cultures Grown in Roller Bottles

Clone #4 was expanded to 34 roller bottles containing a total of 20 L of Hybridoma SFM with 0.4 µM MTX and allowed to reach terminal culture. The supernatant fluid was clarified by centrifugation, filtered (0.2 µM), diafiltered into 1× Binding buffer (10 mM Imidazole, 0.5 M NaCl, 50 mM $NaH_2PO_4$, pH 7.5 and concentrated. The concentrate was purified by IMAC.

Construction and Expression of G-CSF-DDD2 in E. coli.

G-CSF-DDD2 was also expressed by microbial fermentation as a soluble protein in E. coli. The coding sequence was amplified by PCR using G-CSF-DDD2-pdHL2 DNA as a template. The amplimer was cloned into the pET26b E. coli expression vector using Nde I and Xho I restriction sites. Protein was expressed intracellularly in BL21pLysS host cells by induction of LB shake flasks with 100 µM IPTG at 18° C. for 12 hours. Soluble G-CSF-DDD2 was purified from cell lysates by IMAC.

Construction and Expression of N-DDD2-G-CSF(C17S) in E. coli.

An alternative G-CSF-DDD2 module was made by fusing the DDD2 sequence and a peptide spacer at the N-terminus of G-CSF(C17S), which differs from the wild-type by substituting the unpaired cysteine residue at the $17^{th}$ position with a serine. N-DDD2-G-CSF(C17S) was expressed in E. coli and purified by IMAC.

Example 11. Generation of hR1-17S, a DNL Conjugate Comprising Four N-DDD2-G-CSF(C17S) Moieties Linked to $C_{H3}$-AD2-IgG-hR1 hR1-17S was produced by combining $C_{H3}$-AD2-IgG-hR1 with excess N-DDD2-G-CSF(C17S) under redox conditions following purification by Protein A affinity chromatography. SE-HPLC analysis of the protein A-purified hR1-17S showed a major peak and a shoulder of a higher molecular size (not shown). The retention time of the major peak was consistent with a covalent complex composed of an IgG and 4 G-CSF groups. The shoulder was likely due to a non-covalent dimer of the IgG-G-CSF conjugate. SDS-PAGE analysis with Coomassie blue staining and anti-G-CSF immunoblot analysis showed that under non-reducing conditions the product had an Mr consistent with the deduced MW of ~260 kDa. Under reducing conditions, bands representing the three constituent polypeptides of hR1-17S (N-DDD2-G-CSF(C17S), Heavy chain-AD2, and light chain) were detected (not shown).

Example 12. Tetrameric G-CSF with Improved Biological Activity

The Dock-and-Lock (DNL) method was applied to produce three IgG-AD2 fusion proteins, each of which was combined with the dimer of a G-CSF-DDD2 fusion protein to generate a stably tethered complex comprising an intact IgG linked at its CH3 termini to four molecules of G-CSF. The humanized IgGs fused to AD2 were hA20 (anti-CD20), hMN14 (anti-CEACAM5), and h734 (anti-indium-DTPA). In G-CSF-DDD2, the unpaired cysteine (C17) of wild-type G-CSF was replaced with a serine. As expected, a dimeric form of G-CSF-DDD2 was predominantly obtained following purification. Reacting G-CSF-DDD2 to each of the three IgG-AD2 modules resulted in hA20-G-CSF, hMN14-G-CSF and h734-G-CSF, respectively. IgG-G-CSF was purified from the reaction mixture by Protein A chromatography.

Figure 9:
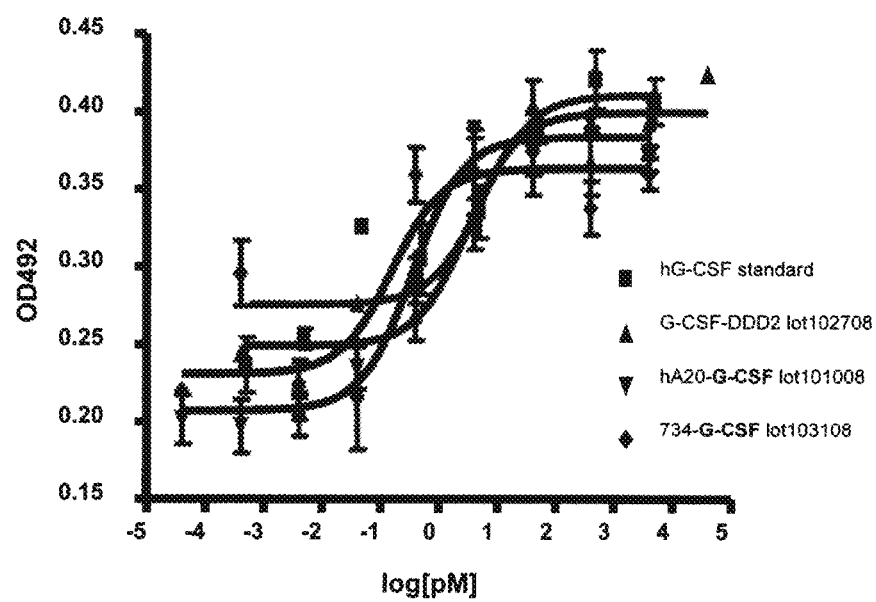
FIG. 9. In vitro proliferation assay with tetrameric G-CSF DNL construct in Kasumi-1 myeloid leukemia cells, showing that IgG-G-CSF complexes are more potent than recombinant hG-CSF.
Figure 10:
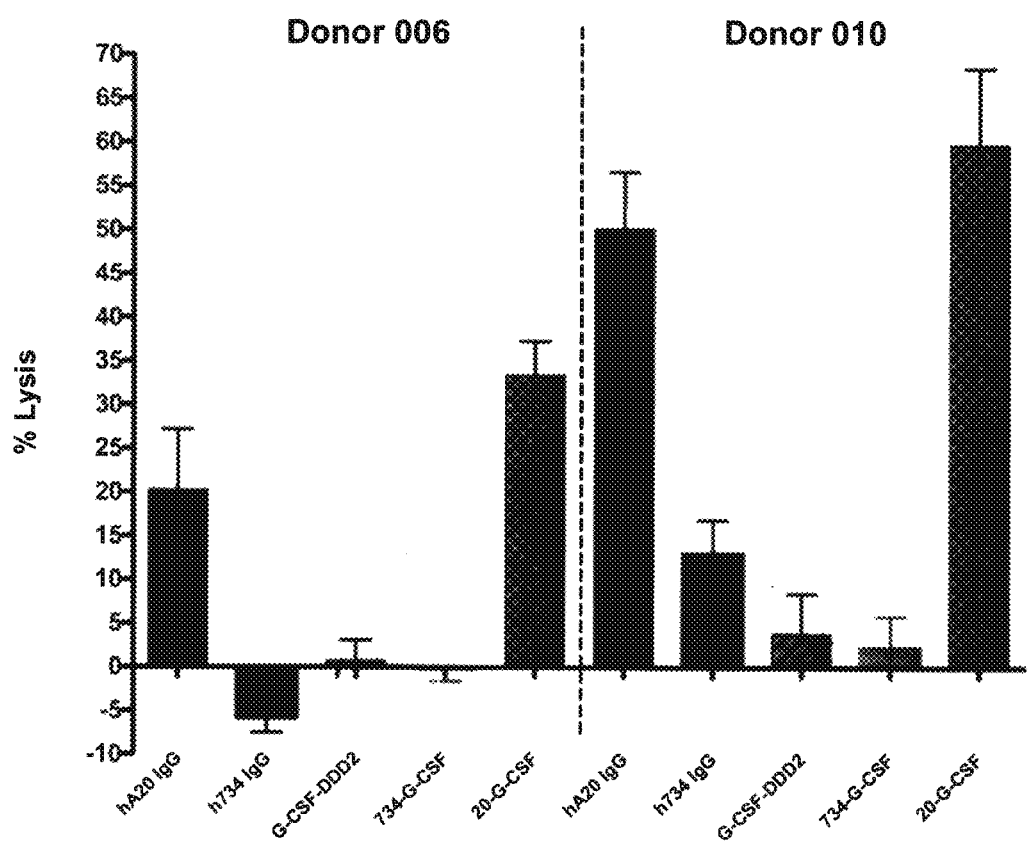
FIG. 10. ADCC activity of hA20-G-CSF DNL construct evaluated in CD20-positive Daudi cells with the PBMCs isolated from two different donors. For both donors, enhanced ADCC was observed for hA20-G-CSF compared to the parental hA20 IgG (veltuzumab): donor 006, 35% vs. 20% (P<0.0191); donor 010, 60% vs. 50% (not statistically significant). The concentration of each agent tested was 5 µg/mL.

The purity, size, and composition of each IgG-G-CSF were confirmed by SDS-PAGE, size-exclusion HPLC, and western blotting (not shown). An in vitro proliferation assay using Kasumi-1 (a myeloid leukemia cell line) showed that IgG-G-CSF complexes were more potent compared with recombinant hG-CSF (FIG. 9). ADCC studies of hA20-G-CSF were performed in CD20-positive Daudi cells with the PBMCs isolated from two different donors (FIG. 10). For both donors, enhanced ADCC was observed for hA20-G-CSF compared to the parental hA20 IgG (veltuzumab): donor 006, 35% vs. 20% (P<0.0191); donor 010, 60% vs. 50% (not statistically significant). The concentration of each agent tested was 5 µg/mL.

Figure 11:
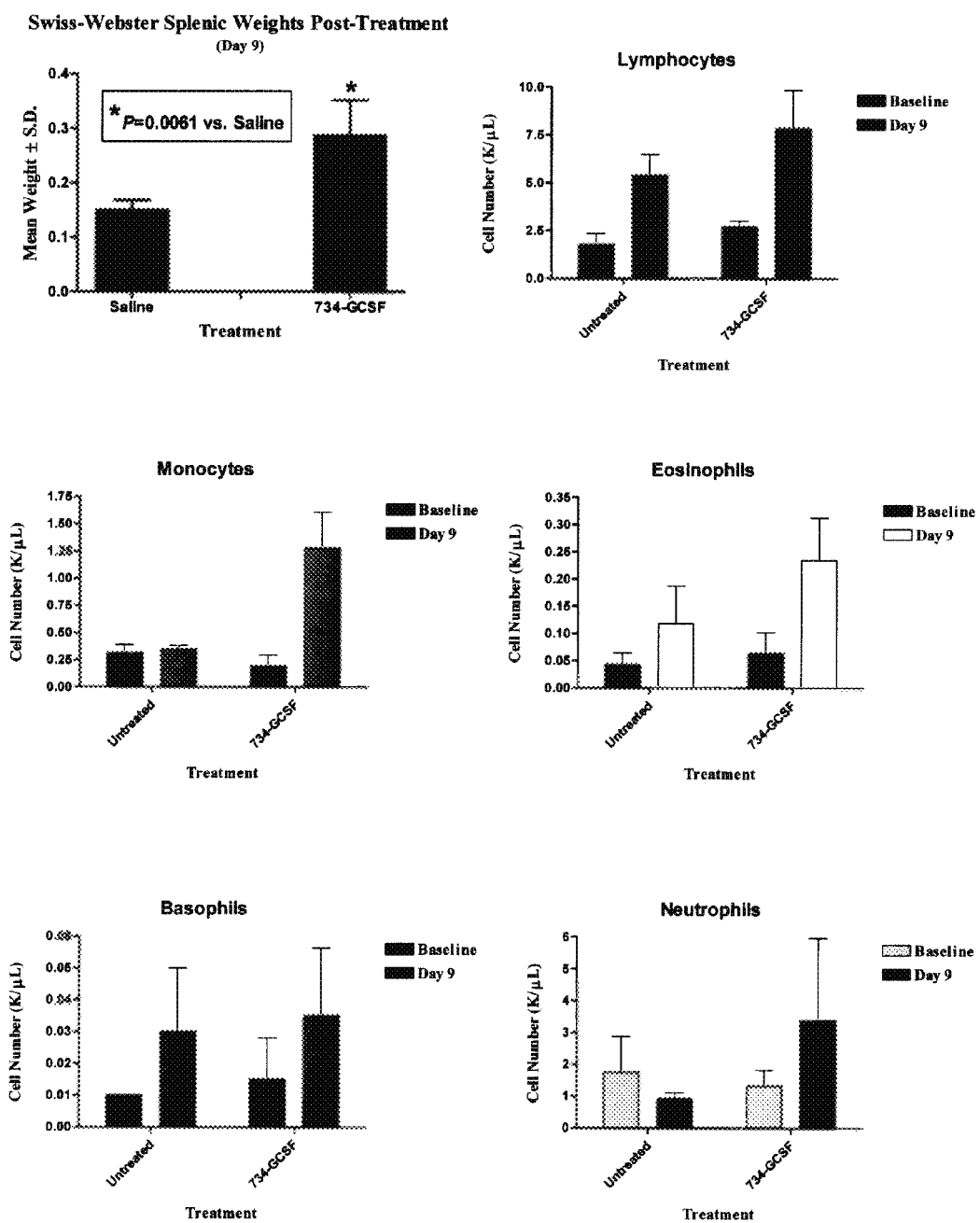
FIG. 11. In vivo activity of G-CSF DNL construct.

In vivo studies in normal mice also revealed the spleen of the treated group had an average weight that was about 2- to 3-times that of the untreated group (P=0.0061) (FIG. 11). In addition, the numbers of monocytes and neutrophils in the blood of the treated mice, when measured at day 9, were increased about 5- and 2-fold, respectively, compared to the untreated mice (FIG. 11). The three IgG-G-CSF complexes represent a novel class of bioactive immunocytokines comprising tetrameric G-CSF anchored onto an IgG, which are expected to show improved pharmacokinetics and additional targeting specificity conferred by the built-in IgG. Because rituximab (anti-CD20) therapy causes neutropenia in patients, the potential of hA20-IgG-G-CSF to enhance the potency of an anti-CD20 antibody yet prevent neutropenia is advantageous.

Example 13. Tetrameric Erythropoietin with Improved Biological Activity

We combined a recombinant fusion protein comprising erythropoietin attached to a DDD sequence with either (1) a recombinant 40 kDa PEG-AD module to generate a PEGylated dimeric Epo; (2) a recombinant Fab-AD module to generate a dimeric Epo-Fab construct; or (3) a recombinant IgG-AD module to generate a tetrameric Epo-IgG conjugate. Epo-DDD2 was generated by recombinant fusion of the DDD2 peptide to the carbodyl terminus of human Epo via an 18 amino acid linker peptide. $C_H1$-AD2-Fab was generated by recombinant fusion of the AD2 peptide to the carboxyl terminus of the $C_H1$ domain of a Fab via a 15 amino acid linker peptide. IMP457 was generated by forming a sulfide linkage between the maleimide group of mPEG2-MAL-40K to the N-terminal cysteine residue of the AD2 peptide IMP 421.

IMP 421
(SEQ ID NO: 31)
Ac-C-PEG$_3$-C(S-tBu)GQIEYLAKQIVDNAIQQAGC(S-tBu)G-NH$_2$

DNL modules for IgG-AD2, Fab-AD2 and Epo-DDD2 were purified from the supernatant fluid of separate recombinant myeloma cultures by Protein A, Protein L and immobilized metal affinity chromatography (IMAC), respectively. Combining an IgG-AD2 module with slightly more than two molar equivalents of Epo-DDD2 module under mild redox conditions resulted in the formation of a covalent complex comprising one IgG and 4 Epo groups via the docking of each of the two AD2 domains on IgG with a dimer of Epo-DDD2, and subsequent formation of disulfide bonds (locking) between DDD2 and AD2. IgG-Epo, which was purified by Protein A following the DNL reaction, was detected by non-reducing SDS-PAGE and size-exclusion HPLC (SE-HPLC), where it was resolved as a single predominant protein peak with a retention time consistent with a 255-kDa protein (not shown). Combining Fab-AD2 and Epo-DDD2 modules by DNL resulted in the formation of a covalent complex comprising one Fab and 2 Epo groups (not shown). Fab-Epo was purified by Protein L and analyzed by non-reducing SDS-PAGE and SE-HPLC, where it was resolved as a single predominant protein peak with a retention time consistent with a 100-kDa protein (not shown). Combining a PEG-AD2 module (IMP457) and Epo-DDD2 resulted in the formation of a covalent complex comprising 40 kDa branched PEG and 2 Epo groups. 457-Epo, which was purified by Q-Sepharose IEC at pH-6, was detected by non-reducing SDS-PAGE with Coomassie blue and Iodine staining (not shown).

Figure 12:
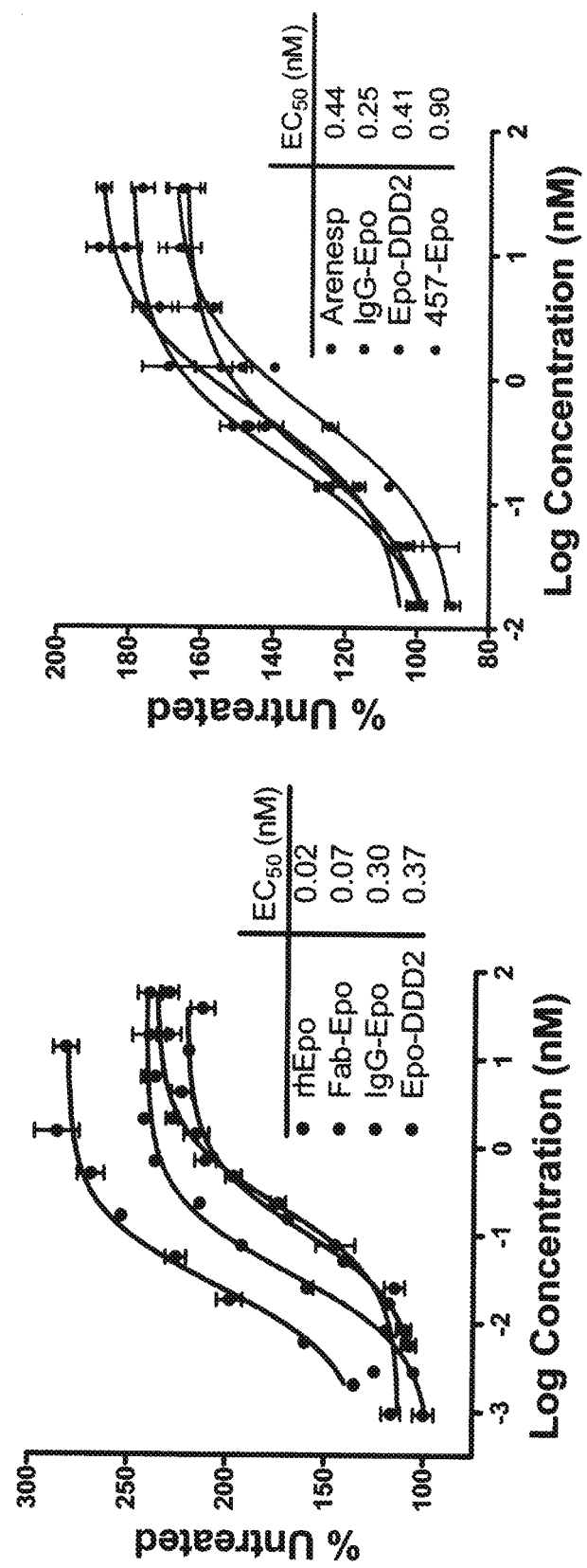
FIG. 12. In vitro potency of Epo DNL constructs, measured by their ability to stimulate proliferation of the cytokine-dependent TF1 cell line. TF1 cells were incubated with serial dilutions of rhEpo, ARANESP®, Epo-DDD2, Fab-Epo, IgG-Epo or 457-Epo. The results show that the Epo-DDD2 module and each DNL construct maintained Epo biological activity with similar specific activity as ARANESP®.

The in vitro potency of various Epo constructs was measured by their ability to stimulate the proliferation of the cytokine-dependent TF1 cell line (FIG. 12). TF1 cells were incubated with serial dilutions of rhEpo, ARANESP®, Epo-DDD2, Fab-Epo, IgG-Epo, or 457-Epo. The results (FIG. 12) show that the Epo-DDD2 module and each DNL construct maintained Epo biological activity. IgG-Epo, Fab-Epo and 457-Epo all stimulated of proliferation of the cytokine-dependent TF1 cell line with similar potency to rhEpo (ARANESP®).

Figure 13:
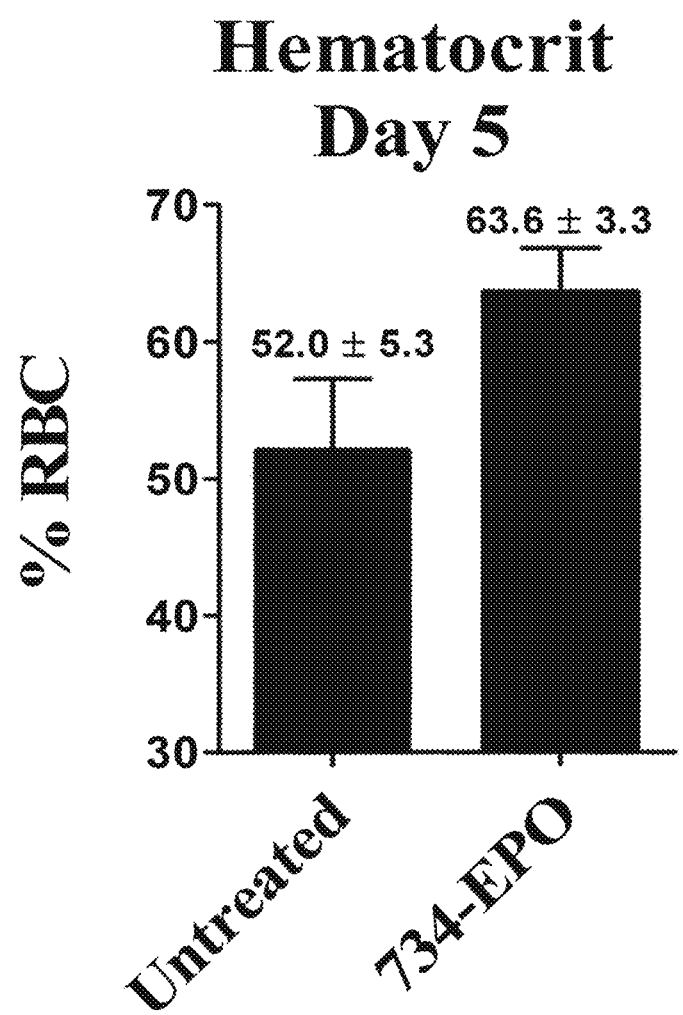
FIG. 13. In vivo activity of Epo DNL construct. Normal Swiss-Webster mice (n=4) were administered a single i.v. injection (3.2 µg) of IgG-Epo and the hematocrit was measured after five days. The results show that treatment with IgG-Epo produced a significant (P=0.0107) increase in hematocrit compared to untreated mice.

In vivo activity of IgG-Epo was determined by its effects on hematocrit levels. Normal Swiss-Webster mice (n=4) were administered a single i.v. injection (3.2 µg) of IgG-Epo and the hematocrit was measured after five days. The results (FIG. 13) showed that a single i.v. administration of IgG-hEpo produced a significant (P=0.0107) increase in hematocrit compared to untreated mice. The DNL method provides a novel approach for efficiently tethering cytokines, such as Epo, to a variety of molecules including IgG, Fab and PEG, which may enhance their in vivo biological activity by improving their pharmacokinetics and stability.

All of the COMPOSITIONS and METHODS disclosed and claimed herein can be made and used without undue experimentation in light of the present disclosure. While the compositions and methods have been described in terms of preferred embodiments, it is apparent to those of skill in the art that variations may be applied to the COMPOSITIONS and METHODS and in the steps or in the sequence of steps of the METHODS described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A cytokine-antibody complex comprising;
   a) a cytokine moiety attached to a DDD (dimerization and docking domain) moiety, wherein the amino acid sequence of said DDD moiety is residues 1-44 of human protein kinase A (PKA) RIIa, wherein the cytokine moiety is selected from the group consisting of MIF (macrophage migration inhibitory factor), IL-1, IL-2, IL-3, IL-4, IL-5, IL-6, IL-7, IL-8, IL-9, IL-10, IL-11, IL-12, IL-13, IL-15, IL-16, IL-17, IL-18, interferon-α, interferon-β, G-CSF, GM-CSF, erythropoietin, and thrombopoietin; and
   b) an antibody moiety attached to an AD (anchor domain) moiety, wherein the amino acid sequence of the AD moiety is from a human AKAP (A-kinase anchoring protein), wherein the DDD moieties form a dimer that binds to the AD moiety to form the complex, wherein the antibody moiety binds to a human antigen selected from the group consisting of carbonic anhydrase IX, CD1, CD1a, CD2, CD3, CD5, CD8, CD14, CD15, CD16, CD19, IGF-1R, CD20, CD21, CD22, CD23, CD25, CD30, CD33, CD37, CD38, CD40, CD45, CD46, CD52, CD55, CD59, CD64, CD70, CD74, CD79a, CD80, CD83, CD95, CD138, CD147, CD154, PSMA, CEACAM5, CEACAM-6, ED-B of fibronectin, Flt-3, folate receptor, HMGB-1 (high mobility group protein B-1), hypoxia inducible factor (HIF), MAGE, MUC1, MUC2, MUC3, MUC4, EGP-1, EGP-2, HLA-DR, tenascin, Le(y), Tn antigen, VEGFR, and EGFR.

2. The complex of claim 1, wherein the antibody moiety is selected from the group consisting of an IgG antibody and an antigen-binding antibody fragment thereof.

3. The complex of claim 1, wherein the antibody moiety is selected from the group consisting of hR1 (anti-IGF-1R), hPAM4 (anti-mucin), hA20 (anti-CD20) hLL1 (anti-CD74), hLL2 (anti-CD22), L243 (anti-HLA-DR), hMN-14 (anti-CEA), hMN-15 (anti-CEA), and hRS7 (anti-EGP-1).

4. The complex of claim 1, wherein the cytokine moiety is selected from the group consisting of interferon (IFN)-α, G-CSF and erythropoietin.

5. The complex of claim 1, wherein the antibody moiety is hA20 IgG antibody and the cytokine moiety is IFNα.

6. The complex of claim 1, the cytokine moiety and the DDD moiety form a first fusion protein and the antibody moiety and the AD moiety form a second fusion protein.

* * * * *

SEQUENCE LISTING

<160> NUMBER OF SEQ ID NOS: 31

<210> SEQ ID NO 1
<211> LENGTH: 44
<212> TYPE: PRT
<213> ORGANISM: Homo sapiens

-continued

```
<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Homo sapiens

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Homo sapiens

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Homo sapiens

<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 5
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
<220> FEATURE:
<221> NAME/KEY: MOD_RES
<222> LOCATION: (6)..(8)
<223> OTHER INFORMATION: Any conservative amino acid substitution
<220> FEATURE:
<221> NAME/KEY: MOD_RES
<222> LOCATION: (10)..(11)
```

```
<223> OTHER INFORMATION: Any conservative amino acid substitution
<220> FEATURE:
<221> NAME/KEY: MOD_RES
<222> LOCATION: (14)..(15)
<223> OTHER INFORMATION: Any conservative amino acid substitution
<220> FEATURE:
<221> NAME/KEY: MOD_RES
<222> LOCATION: (17)..(17)
<223> OTHER INFORMATION: Any conservative amino acid substitution
<220> FEATURE:
<221> NAME/KEY: MOD_RES
<222> LOCATION: (19)..(19)
<223> OTHER INFORMATION: Any conservative amino acid substitution
<220> FEATURE:
<221> NAME/KEY: MOD_RES
<222> LOCATION: (22)..(27)
<223> OTHER INFORMATION: Any conservative amino acid substitution
<220> FEATURE:
<221> NAME/KEY: MOD_RES
<222> LOCATION: (30)..(30)
<223> OTHER INFORMATION: Any conservative amino acid substitution
<220> FEATURE:
<221> NAME/KEY: MOD_RES
<222> LOCATION: (32)..(32)
<223> OTHER INFORMATION: Any conservative amino acid substitution
<220> FEATURE:
<221> NAME/KEY: MOD_RES
<222> LOCATION: (34)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(44)
<223> OTHER INFORMATION: Any conservative amino acid substitution

<400> SEQUENCE: 5

Xaa Xaa Ile Xaa Ile Xaa Xaa Xaa Leu Xaa Xaa Leu Leu Xaa Xaa Tyr
1               5                   10                  15

Xaa Val Xaa Val Leu Xaa Xaa Xaa Xaa Xaa Xaa Leu Val Xaa Phe Xaa
            20                  25                  30

Val Xaa Tyr Phe Xaa Xaa Leu Xaa Xaa Xaa Xaa Xaa
        35                  40

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any conservative amino acid substitution
<220> FEATURE:
<221> NAME/KEY: MOD_RES
<222> LOCATION: (7)..(8)
<223> OTHER INFORMATION: Any conservative amino acid substitution
<220> FEATURE:
<221> NAME/KEY: MOD_RES
<222> LOCATION: (11)..(12)
<223> OTHER INFORMATION: Any conservative amino acid substitution
<220> FEATURE:
<221> NAME/KEY: MOD_RES
<222> LOCATION: (15)..(17)
<223> OTHER INFORMATION: Any conservative amino acid substitution

<400> SEQUENCE: 6

Xaa Xaa Xaa Xaa Xaa Ala Xaa Xaa Ile Val Xaa Xaa Ala Ile Xaa Xaa
1               5                   10                  15
```

Xaa

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ile Glu Tyr Val Ala Lys Gln Ile Val Asp Tyr Ala Ile His Gln
1               5                   10                  15

Ala

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ile Glu Tyr Lys Ala Lys Gln Ile Val Asp His Ala Ile His Gln
1               5                   10                  15

Ala

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ile Glu Tyr His Ala Lys Gln Ile Val Asp His Ala Ile His Gln
1               5                   10                  15

Ala

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ile Glu Tyr Val Ala Lys Gln Ile Val Asp His Ala Ile His Gln
1               5                   10                  15

Ala

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Leu Ile Glu Glu Ala Ala Ser Arg Ile Val Asp Ala Val Ile Glu
1               5                   10                  15

```
Gln Val Lys Ala Ala Gly Ala Tyr
            20

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Glu Gln Tyr Ala Asn Gln Leu Ala Asp Gln Ile Ile Lys Glu Ala
1               5                   10                  15

Thr Glu

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Glu Glu Leu Ala Trp Lys Ile Ala Lys Met Ile Trp Ser Asp Val
1               5                   10                  15

Phe Gln Gln Cys
            20

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 16

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
<220> FEATURE:
<221> NAME/KEY: MOD_RES
<222> LOCATION: (7)..(7)
<223> OTHER INFORMATION: Any conservative amino acid substitution
<220> FEATURE:
<221> NAME/KEY: MOD_RES
<222> LOCATION: (10)..(10)
<223> OTHER INFORMATION: Any conservative amino acid substitution
<220> FEATURE:
<221> NAME/KEY: MOD_RES
<222> LOCATION: (18)..(18)
<223> OTHER INFORMATION: Any conservative amino acid substitution
<220> FEATURE:
<221> NAME/KEY: MOD_RES
<222> LOCATION: (23)..(23)
<223> OTHER INFORMATION: Any conservative amino acid substitution
<220> FEATURE:
<221> NAME/KEY: MOD_RES
<222> LOCATION: (26)..(26)
<223> OTHER INFORMATION: Any conservative amino acid substitution
<220> FEATURE:
<221> NAME/KEY: MOD_RES
<222> LOCATION: (33)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(40)
<223> OTHER INFORMATION: Any conservative amino acid substitution
<220> FEATURE:
<221> NAME/KEY: MOD_RES
<222> LOCATION: (42)..(42)
<223> OTHER INFORMATION: Any conservative amino acid substitution
<220> FEATURE:
<221> NAME/KEY: MOD_RES
<222> LOCATION: (44)..(44)
<223> OTHER INFORMATION: Any conservative amino acid substitution

<400> SEQUENCE: 17

Xaa His Ile Xaa Ile Pro Xaa Gly Leu Xaa Glu Leu Leu Gln Gly Tyr
1               5                   10                  15

Thr Xaa Glu Val Leu Arg Xaa Gln Pro Xaa Asp Leu Val Glu Phe Ala
            20                  25                  30

Xaa Xaa Tyr Phe Xaa Xaa Leu Xaa Glu Xaa Arg Xaa
        35                  40

<210> SEQ ID NO 18

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Lys Ser Leu Ser Leu Ser Pro Gly Leu Gly Ser Gly Gly Gly Gly
1               5                   10                  15

Ser Gly Gly Cys Gly
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Lys Ser Leu Ser Leu Ser Pro Gly Ala Gly Ser Gly Gly Gly Gly
1               5                   10                  15

Ser Gly Gly Cys Gly
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Lys Ser Leu Ser Leu Ser Pro Gly Gly Ser Gly Gly Gly Gly Ser
1               5                   10                  15

Gly Gly Cys Gly
            20

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agatctggcg cacctgaact cctg                                          24

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaattcggat cctttacccg gagacaggga gag                                33

<210> SEQ ID NO 23
<211> LENGTH: 63
<212> TYPE: PRT
```

<213> ORGANISM: Artificial Sequence
<220> FEATURE:
<223> OTHER INFORMATION: Description of Artificial Sequence: Synthetic
    polypeptide

<400> SEQUENCE: 23

Lys Ser His His His His His His Gly Ser Gly Gly Gly Ser Gly
1               5                   10                  15

Gly Gly Cys Gly His Ile Gln Ile Pro Pro Gly Leu Thr Glu Leu Leu
            20                  25                  30

Gln Gly Tyr Thr Val Glu Val Leu Arg Gln Gln Pro Pro Asp Leu Val
        35                  40                  45

Glu Phe Ala Val Glu Tyr Phe Thr Arg Leu Arg Glu Ala Arg Ala
    50                  55                  60

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 24
tctagacaca ggacctcatc atggccttga cctttgcttt actgg                45

<210> SEQ ID NO 25
<211> LENGTH: 55
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 25
ggatccatga tggtgatgat ggtgtgactt ttccttactt cttaaactttt cttgc      55

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 26
tctagacaca ggacctcatc atgggggtgc acgaatgtcc                       40

<210> SEQ ID NO 27
<211> LENGTH: 49
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 27
ggatccatga tggtgatgat ggtgtgactt tctgtccct gtcctgcag              49

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
    6xHis tag

<400> SEQUENCE: 28

His His His His His His
1               5

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tctagacaca ggacctcatc atggctggac ctgccaccca g                    41

<210> SEQ ID NO 30
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggatccatga tggtgatgat ggtgtgactt gggctgggca aggtggcgta g          51

<210> SEQ ID NO 31
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Cys-PEG3
<220> FEATURE:
<221> NAME/KEY: MOD_RES
<222> LOCATION: (2)..(2)
<223> OTHER INFORMATION: Cys(S-tBu)
<220> FEATURE:
<221> NAME/KEY: MOD_RES
<222> LOCATION: (22)..(22)
<223> OTHER INFORMATION: Cys(S-tBu)
<220> FEATURE:
<223> OTHER INFORMATION: C-term amidated

<400> SEQUENCE: 31

Cys Cys Gly Gln Ile Glu Tyr Leu Ala Lys Gln Ile Val Asp Asn Ala
1               5                   10                  15

Ile Gln Gln Ala Gly Cys Gly
            20